(12) United States Patent
Luc et al.

(10) Patent No.: US 9,108,782 B2
(45) Date of Patent: Aug. 18, 2015

(54) DISPENSING SYSTEMS WITH IMPROVED SENSING CAPABILITIES

(71) Applicant: S.C. Johnson & Son, Inc., Racine, WI (US)

(72) Inventors: Tai P. Luc, Oak Creek, WI (US); Claudia V. Gamboa, Northfield, IL (US); Mark E. Johnson, Racine, WI (US); Daniel J. Hanak, Milwaukee, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 5 days.

(21) Appl. No.: 13/652,388

(22) Filed: Oct. 15, 2012

(65) Prior Publication Data

US 2014/0103479 A1 Apr. 17, 2014

(51) Int. Cl.
*G08B 23/00* (2006.01)
*B65D 83/00* (2006.01)
*A61L 9/12* (2006.01)
*A61L 9/14* (2006.01)

(52) U.S. Cl.
CPC . *B65D 83/00* (2013.01); *A61L 9/12* (2013.01); *A61L 9/14* (2013.01); *A61L 2209/111* (2013.01); *A61L 2209/133* (2013.01)

(58) Field of Classification Search
CPC ............ B65D 83/00; A61L 9/12; A61L 9/14; A61L 2209/111; A61L 2209/133; H05K 5/0247
USPC .......................... 222/52, 63; 340/693.6; 53/74
See application file for complete search history.

(56) References Cited

U.S. PATENT DOCUMENTS

| | | | |
|---|---|---|---|
| 2,550,825 | A | 5/1951 | Kolodie |
| 2,613,108 | A | 10/1952 | Krause |
| 2,928,573 | A | 3/1960 | Edelstein |
| 2,971,382 | A | 2/1961 | Harris |
| 2,991,912 | A | 7/1961 | Thomas et al. |
| 3,018,056 | A | 1/1962 | Montgomery |
| 3,127,060 | A | 3/1964 | Vosbikian et al. |
| 3,138,331 | A | 6/1964 | Kutik |
| 3,165,238 | A | 1/1965 | Willey |
| 3,185,356 | A | 5/1965 | Venus, Jr. |
| 3,187,948 | A | 6/1965 | Hunt |
| 3,187,949 | A | 6/1965 | Mangel |
| 3,199,732 | A | 8/1965 | Strachan |
| 3,214,062 | A | 10/1965 | Mahon |
| 3,228,609 | A | 1/1966 | Edelstein et al. |
| 3,240,389 | A | 3/1966 | Genua |

(Continued)

FOREIGN PATENT DOCUMENTS

| | | |
|---|---|---|
| AR | 056799 | 11/2006 |
| AU | 591829 | 9/1989 |

(Continued)

OTHER PUBLICATIONS

JP 2006-159071—English Translation Jan. 2014.*

(Continued)

*Primary Examiner* — J. Casimer Jacyna
*Assistant Examiner* — Benjamin R Shaw

(57) ABSTRACT

A dispensing system includes a dispenser, at least one sensor, and a shroud including at least one aperture. A virtual shield is provided between the sensor and the shroud to reduce background noise.

18 Claims, 19 Drawing Sheets

(56) References Cited

U.S. PATENT DOCUMENTS

| | | | |
|---|---|---|---|
| 3,289,886 A | 12/1966 | Goldsholl et al. | |
| 3,305,134 A | 2/1967 | Carmichael et al. | |
| 3,326,418 A | 6/1967 | Kropp | |
| 3,368,717 A | 2/1968 | Weber | |
| 3,369,697 A | 2/1968 | Glucksman et al. | |
| 3,388,834 A | 6/1968 | Hart | |
| 3,398,863 A | 8/1968 | Kolodziej | |
| 3,398,864 A | 8/1968 | Kolodziej | |
| 3,419,189 A | 12/1968 | Iketani | |
| 3,472,457 A | 10/1969 | McAvoy | |
| 3,477,613 A | 11/1969 | Mangel | |
| 3,497,108 A | 2/1970 | Mason | |
| 3,498,504 A | 3/1970 | Wilkins | |
| 3,542,248 A | 11/1970 | Mangel | |
| 3,543,122 A | 11/1970 | Klebanoff et al. | |
| 3,584,766 A | 6/1971 | Hart | |
| 3,587,332 A | 6/1971 | Bell | |
| 3,589,563 A | 6/1971 | Carragan et al. | |
| 3,610,471 A | 10/1971 | Werner | |
| 3,615,041 A | 10/1971 | Bischoff | |
| 3,617,214 A | 11/1971 | Dolac | |
| 3,627,176 A | 12/1971 | Sailors | |
| 3,643,836 A | 2/1972 | Hunt | |
| 3,658,209 A | 4/1972 | Freeman et al. | |
| 3,664,548 A | 5/1972 | Broderick | |
| 3,666,144 A | 5/1972 | Winder | |
| 3,677,441 A | 7/1972 | Nixon, Jr. et al. | |
| 3,726,437 A | 4/1973 | Siegel | |
| 3,732,509 A | 5/1973 | Florant et al. | |
| 3,739,944 A | 6/1973 | Rogerson | |
| 3,758,002 A | 9/1973 | Doyle et al. | |
| 3,779,425 A | 12/1973 | Werner | |
| 3,784,061 A | 1/1974 | Hogan | |
| 3,817,429 A | 6/1974 | Smrt | |
| 3,841,525 A | 10/1974 | Siegel | |
| 3,856,443 A | 12/1974 | Salvi | |
| 3,865,275 A | 2/1975 | De Nunzio | |
| 3,870,274 A | 3/1975 | Broe | |
| 3,929,259 A | 12/1975 | Fegley et al. | |
| 3,952,916 A | 4/1976 | Phillips | |
| 3,968,905 A | 7/1976 | Pelton | |
| 3,974,941 A | 8/1976 | Mettler | |
| 3,980,205 A | 9/1976 | Smart | |
| RE29,117 E | 1/1977 | Sahajian et al. | |
| 4,004,550 A | 1/1977 | White et al. | |
| 4,004,715 A | 1/1977 | Williams et al. | |
| 4,006,844 A | 2/1977 | Corris | |
| 4,011,927 A | 3/1977 | Smith | |
| 4,063,664 A | 12/1977 | Meetze, Jr. | |
| 4,068,575 A | 1/1978 | Difley et al. | |
| 4,068,780 A | 1/1978 | Fegley | |
| 4,077,542 A | 3/1978 | Petterson | |
| 4,184,612 A | 1/1980 | Freyre | |
| 4,235,373 A | 11/1980 | Clark | |
| 4,238,055 A | 12/1980 | Staar | |
| 4,307,388 A * | 12/1981 | Doenges et al. | 340/567 |
| 4,396,152 A | 8/1983 | Abplanalp | |
| 4,483,466 A | 11/1984 | Gutierrez | |
| 4,544,086 A | 10/1985 | Hill et al. | |
| 4,572,410 A | 2/1986 | Brunet | |
| 4,636,091 A * | 1/1987 | Pompei et al. | 374/124 |
| 4,666,638 A | 5/1987 | Baker et al. | |
| 4,671,435 A | 6/1987 | Stout et al. | |
| 4,690,312 A | 9/1987 | Crapser et al. | |
| 4,695,435 A * | 9/1987 | Spector | 422/124 |
| 4,742,583 A | 5/1988 | Yoshida et al. | |
| 4,798,935 A | 1/1989 | Pezaris | |
| 4,801,093 A | 1/1989 | Brunet et al. | |
| 4,816,951 A | 3/1989 | Zago | |
| 4,830,791 A | 5/1989 | Muderlak et al. | |
| 4,836,420 A | 6/1989 | Kromrey | |
| 4,852,802 A | 8/1989 | Iggulden et al. | |
| 4,877,989 A | 10/1989 | Drews et al. | |
| 4,916,762 A | 4/1990 | Shaw | |
| 4,967,935 A | 11/1990 | Celest | |
| 4,989,755 A | 2/1991 | Shiau | |
| 5,014,881 A | 5/1991 | Andris | |
| 5,014,884 A | 5/1991 | Wunsch | |
| 5,018,963 A | 5/1991 | Diederich | |
| 5,022,557 A | 6/1991 | Turner | |
| 5,025,516 A * | 6/1991 | Wilson | 4/623 |
| 5,025,962 A | 6/1991 | Renfro | |
| 5,055,822 A | 10/1991 | Campbell et al. | |
| 5,105,133 A | 4/1992 | Yang | |
| 5,134,961 A | 8/1992 | Giles et al. | |
| 5,175,791 A | 12/1992 | Muderlak et al. | |
| 5,198,157 A | 3/1993 | Bechet | |
| 5,221,025 A | 6/1993 | Privas | |
| 5,230,837 A | 7/1993 | Babasade | |
| 5,243,326 A * | 9/1993 | Disabato | 340/555 |
| 5,249,718 A | 10/1993 | Muderlak | |
| 5,269,445 A | 12/1993 | Tobler | |
| 5,337,926 A | 8/1994 | Drobish et al. | |
| 5,337,929 A | 8/1994 | van der Heijden | |
| 5,342,584 A | 8/1994 | Fritz et al. | |
| 5,349,945 A | 9/1994 | Wass et al. | |
| 5,353,546 A | 10/1994 | Bock | |
| 5,353,744 A | 10/1994 | Custer | |
| 5,358,147 A | 10/1994 | Adams et al. | |
| 5,383,580 A | 1/1995 | Winder | |
| RE34,847 E * | 2/1995 | Muderlak et al. | 222/25 |
| 5,392,768 A | 2/1995 | Johansson et al. | |
| 5,394,866 A | 3/1995 | Ritson et al. | |
| 5,397,028 A | 3/1995 | Jesadanont | |
| 5,434,386 A | 7/1995 | Glenn et al. | |
| 5,445,324 A | 8/1995 | Berry et al. | |
| 5,449,117 A | 9/1995 | Muderlak et al. | |
| 5,450,336 A | 9/1995 | Rubsamen et al. | |
| 5,487,502 A | 1/1996 | Liao | |
| 5,489,047 A | 2/1996 | Winder | |
| 5,497,764 A | 3/1996 | Ritson et al. | |
| 5,499,016 A * | 3/1996 | Pantus | 340/555 |
| 5,503,303 A | 4/1996 | LaWare et al. | |
| 5,520,166 A | 5/1996 | Ritson et al. | |
| 5,522,378 A | 6/1996 | Ritson et al. | |
| 5,531,344 A | 7/1996 | Winner | |
| 5,542,605 A | 8/1996 | Campau | |
| 5,547,721 A | 8/1996 | Kuo | |
| 5,591,409 A | 1/1997 | Watkins | |
| 5,622,162 A | 4/1997 | Johansson et al. | |
| 5,647,388 A | 7/1997 | Butler, Jr. et al. | |
| 5,657,910 A | 8/1997 | Keyser | |
| 5,673,825 A | 10/1997 | Chen | |
| 5,676,283 A | 10/1997 | Wang | |
| 5,685,456 A | 11/1997 | Goldstein | |
| 5,695,091 A | 12/1997 | Winings et al. | |
| 5,699,243 A | 12/1997 | Eckel et al. | |
| 5,702,036 A | 12/1997 | Ferrara | |
| 5,735,918 A | 4/1998 | Barradas | |
| 5,743,251 A | 4/1998 | Howell et al. | |
| 5,743,252 A | 4/1998 | Rubsamen et al. | |
| 5,755,218 A | 5/1998 | Johansson et al. | |
| 5,772,074 A | 6/1998 | Dial et al. | |
| 5,787,947 A | 8/1998 | Hertsgaard | |
| 5,791,524 A | 8/1998 | Demarest | |
| 5,804,827 A * | 9/1998 | Akagawa et al. | 250/370.06 |
| 5,806,697 A | 9/1998 | Harbutt et al. | |
| 5,810,265 A | 9/1998 | Cornelius et al. | |
| 5,811,766 A | 9/1998 | Fabrikant et al. | |
| 5,823,390 A | 10/1998 | Muderlak et al. | |
| 5,826,570 A | 10/1998 | Goodman et al. | |
| 5,853,129 A | 12/1998 | Spitz | |
| 5,862,844 A * | 1/1999 | Perrin | 141/351 |
| 5,884,808 A | 3/1999 | Muderlak et al. | |
| 5,908,140 A | 6/1999 | Muderlak | |
| 5,922,247 A | 7/1999 | Shoham et al. | |
| 5,924,597 A | 7/1999 | Lynn | |
| 5,924,606 A | 7/1999 | Huizing | |
| 5,938,076 A | 8/1999 | Ganzeboom | |
| 5,946,209 A | 8/1999 | Eckel et al. | |
| 5,962,930 A | 10/1999 | Cluff et al. | |
| 5,964,403 A | 10/1999 | Miller et al. | |
| 6,000,658 A | 12/1999 | McCall, Jr. | |
| 6,006,957 A | 12/1999 | Kunesh | |

(56) References Cited

U.S. PATENT DOCUMENTS

| | | |
|---|---|---|
| 6,026,987 A | 2/2000 | Burnett et al. |
| 6,029,659 A | 2/2000 | O'Connor |
| 6,036,108 A | 3/2000 | Chen |
| 6,039,212 A | 3/2000 | Singh |
| 6,092,912 A | 7/2000 | Nelson |
| 6,142,339 A | 11/2000 | Blacker et al. |
| 6,151,529 A | 11/2000 | Batko |
| 6,158,486 A | 12/2000 | Olson et al. |
| 6,161,724 A | 12/2000 | Blacker et al. |
| 6,182,904 B1 | 2/2001 | Ulczynski et al. |
| 6,196,218 B1 | 3/2001 | Voges |
| 6,206,238 B1 | 3/2001 | Ophardt |
| 6,216,925 B1 | 4/2001 | Garon |
| 6,220,293 B1 | 4/2001 | Rashidi |
| 6,237,461 B1 | 5/2001 | Poole |
| 6,237,812 B1 | 5/2001 | Fukada |
| 6,249,717 B1 | 6/2001 | Nicholson et al. |
| 6,254,065 B1 | 7/2001 | Ehrensperger et al. |
| 6,264,548 B1 | 7/2001 | Payne, Jr. et al. |
| 6,267,297 B1 | 7/2001 | Contadini et al. |
| 6,293,442 B1 | 9/2001 | Mollayan |
| 6,296,172 B1 | 10/2001 | Miller |
| 6,297,297 B1 | 10/2001 | Brookman et al. |
| 6,343,714 B1 | 2/2002 | Tichenor |
| 6,347,414 B2 | 2/2002 | Contadini et al. |
| 6,357,726 B1 | 3/2002 | Watkins |
| 6,361,752 B1 | 3/2002 | Demarest et al. |
| 6,371,450 B1 | 4/2002 | Davis et al. |
| 6,390,453 B1 | 5/2002 | Frederickson et al. |
| 6,394,153 B2 | 5/2002 | Skell et al. |
| 6,394,310 B1 | 5/2002 | Muderlak et al. |
| 6,409,093 B2 | 6/2002 | Ulczynski et al. |
| 6,415,957 B1 | 7/2002 | Michaels et al. |
| 6,419,122 B1 | 7/2002 | Chown |
| 6,446,583 B2 | 9/2002 | Vieira |
| 6,454,127 B1 | 9/2002 | Suomela et al. |
| 6,454,185 B2 | 9/2002 | Fuchs |
| RE37,888 E | 10/2002 | Cretu-Petra |
| 6,461,325 B1 | 10/2002 | Delmotte et al. |
| 6,478,199 B1 | 11/2002 | Shanklin et al. |
| 6,499,900 B1 | 12/2002 | Brozell |
| 6,510,561 B1 | 1/2003 | Hammond et al. |
| 6,516,796 B1 | 2/2003 | Cox et al. |
| 6,517,009 B2 | 2/2003 | Yahav |
| 6,529,446 B1 | 3/2003 | de la Huerga |
| 6,533,141 B1 | 3/2003 | Petterson et al. |
| 6,540,155 B1 | 4/2003 | Yahav |
| 6,554,203 B2 | 4/2003 | Hess et al. |
| 6,567,613 B2 | 5/2003 | Rymer |
| 6,588,627 B2 | 7/2003 | Petterson et al. |
| RE38,207 E | 8/2003 | Benoist |
| 6,607,102 B1 | 8/2003 | Griese et al. |
| 6,610,254 B1 | 8/2003 | Furner et al. |
| 6,612,464 B2 | 9/2003 | Petterson et al. |
| 6,619,562 B2 | 9/2003 | Hamaguchi et al. |
| 6,644,507 B2 | 11/2003 | Borut et al. |
| 6,669,105 B2 | 12/2003 | Bryan et al. |
| 6,672,129 B1 | 1/2004 | Frederickson et al. |
| 6,688,492 B2 | 2/2004 | Jaworski et al. |
| 6,694,536 B1 | 2/2004 | Haygreen |
| 6,698,616 B2 | 3/2004 | Hidle et al. |
| 6,712,287 B1 | 3/2004 | Le Pesant et al. |
| 6,722,529 B2 | 4/2004 | Ceppaluni et al. |
| 6,739,479 B2 | 5/2004 | Contadini et al. |
| 6,769,580 B2 | 8/2004 | Muderlak et al. |
| 6,785,911 B1 | 9/2004 | Percher |
| 6,790,408 B2 | 9/2004 | Whitby et al. |
| 6,795,645 B2 | 9/2004 | Hygema et al. |
| 6,830,164 B2 | 12/2004 | Michaels et al. |
| 6,832,701 B2 | 12/2004 | Schiller |
| 6,834,847 B2 | 12/2004 | Bartsch et al. |
| 6,837,396 B2 | 1/2005 | Jaworski et al. |
| 6,843,465 B1 | 1/2005 | Scott |
| 6,877,636 B2 | 4/2005 | Speckhart et al. |
| 6,877,924 B1 | 4/2005 | Mears et al. |
| 6,889,872 B2 | 5/2005 | Herman et al. |
| 6,903,654 B2 | 6/2005 | Hansen et al. |
| 6,926,002 B2 | 8/2005 | Scarrott et al. |
| 6,926,172 B2 | 8/2005 | Jaworski et al. |
| 6,926,211 B2 | 8/2005 | Bryan et al. |
| 6,929,154 B2 | 8/2005 | Grey et al. |
| 6,938,796 B2 | 9/2005 | Blacker et al. |
| 6,948,192 B2 | 9/2005 | Hipponsteel |
| 6,968,982 B1 | 11/2005 | Burns |
| 6,971,560 B1 | 12/2005 | Healy et al. |
| 6,974,091 B2 | 12/2005 | McLisky |
| 6,978,914 B2 | 12/2005 | Furner et al. |
| 6,978,947 B2 | 12/2005 | Jin |
| 6,981,499 B2 | 1/2006 | Anderson et al. |
| 6,997,349 B2 | 2/2006 | Blacker et al. |
| 7,000,853 B2 | 2/2006 | Fugere |
| 7,011,795 B2 | 3/2006 | Thompson et al. |
| 7,021,499 B2 | 4/2006 | Hansen et al. |
| 7,032,782 B1 | 4/2006 | Ciavarella et al. |
| 7,160,515 B2 | 1/2007 | Murdell et al. |
| 7,168,273 B2 | 1/2007 | Neergaard et al. |
| 7,182,227 B2 | 2/2007 | Poile et al. |
| 7,188,485 B2 | 3/2007 | Szpekman |
| 7,195,139 B2 | 3/2007 | Jaworski et al. |
| 7,201,294 B2 | 4/2007 | Carlucci et al. |
| 7,207,500 B2 | 4/2007 | Hudson et al. |
| 7,215,084 B1 | 5/2007 | Sharrah et al. |
| 7,222,758 B1 | 5/2007 | Scheindel |
| 7,222,760 B1 | 5/2007 | Tsay |
| 7,223,166 B2 | 5/2007 | Wiseman, Sr. et al. |
| 7,223,361 B2 | 5/2007 | Kvietok et al. |
| 7,265,673 B2 | 9/2007 | Teller |
| 7,296,765 B2 | 11/2007 | Rodrian |
| 7,299,953 B2 | 11/2007 | McLisky |
| 7,306,167 B2 | 12/2007 | Colarusso et al. |
| 7,308,790 B1 | 12/2007 | Bennett |
| 7,320,418 B2 | 1/2008 | Sassoon |
| 7,341,169 B2 | 3/2008 | Bayer |
| 7,344,123 B2 | 3/2008 | Pankhurst et al. |
| 7,365,810 B2 | 4/2008 | Gotoh et al. |
| 7,398,013 B2 | 7/2008 | He et al. |
| 7,407,065 B2 | 8/2008 | Hooks et al. |
| 7,437,930 B2 | 10/2008 | Lasserre et al. |
| 7,461,650 B1 | 12/2008 | Rand |
| 7,481,380 B2 | 1/2009 | Kvietok et al. |
| 7,497,354 B2 | 3/2009 | Decottignies et al. |
| 7,509,955 B2 | 3/2009 | Cole et al. |
| 7,538,473 B2 | 5/2009 | Blandino et al. |
| 7,540,433 B2 | 6/2009 | Fleming et al. |
| 7,556,210 B2 | 7/2009 | Mandell et al. |
| 7,584,907 B2 | 9/2009 | Contadini et al. |
| 7,597,099 B2 | 10/2009 | Jones et al. |
| 7,610,118 B2 | 10/2009 | Schramm et al. |
| 7,611,253 B2 | 11/2009 | Chien |
| 7,619,202 B2 * | 11/2009 | Yu .................................. 250/215 |
| 7,628,339 B2 | 12/2009 | Ivri et al. |
| 7,654,416 B2 | 2/2010 | Buining et al. |
| 7,661,562 B2 | 2/2010 | Tyrrell et al. |
| 7,670,479 B2 | 3/2010 | Arett et al. |
| 7,673,820 B2 | 3/2010 | Ivri et al. |
| 7,686,191 B1 | 3/2010 | Burns |
| 7,687,744 B2 | 3/2010 | Walter et al. |
| 7,690,530 B2 | 4/2010 | Schneider et al. |
| 7,722,807 B2 | 5/2010 | Keller, Jr. et al. |
| 7,735,694 B2 | 6/2010 | Brown et al. |
| 7,739,479 B2 | 6/2010 | Bordes et al. |
| 7,740,395 B2 | 6/2010 | Samuel et al. |
| 7,762,714 B2 | 7/2010 | Freeman et al. |
| 7,766,194 B2 | 8/2010 | Boll et al. |
| 7,798,420 B2 | 9/2010 | Lind et al. |
| 7,798,424 B2 | 9/2010 | Lin |
| 7,837,065 B2 | 11/2010 | Furner et al. |
| 7,871,020 B2 | 1/2011 | Nelson et al. |
| 7,893,829 B2 | 2/2011 | Sipinski et al. |
| 7,909,209 B2 | 3/2011 | Reynolds et al. |
| 7,930,068 B2 | 4/2011 | Robert et al. |
| 7,954,667 B2 | 6/2011 | Furner et al. |
| 7,963,475 B2 | 6/2011 | Rodrian |
| 7,979,723 B2 | 7/2011 | Dooley et al. |

(56) References Cited

U.S. PATENT DOCUMENTS

| | | | |
|---|---|---|---|
| 7,981,367 B2 | 7/2011 | Kvietok et al. | |
| 7,995,295 B2 | 8/2011 | Chen | |
| 7,998,403 B2 | 8/2011 | Uchiyama et al. | |
| 8,016,207 B2 | 9/2011 | Kvietok et al. | |
| 8,051,282 B2 | 11/2011 | Sipinski et al. | |
| 8,052,934 B2 | 11/2011 | Manne | |
| 8,061,562 B2 | 11/2011 | Carpenter et al. | |
| 8,074,836 B2 | 12/2011 | Reynolds et al. | |
| 8,074,970 B2 | 12/2011 | Pankhurst et al. | |
| 8,091,734 B2 | 1/2012 | Furner et al. | |
| 8,119,064 B2 | 2/2012 | Woo et al. | |
| 8,170,405 B2 | 5/2012 | Harris | |
| 8,177,102 B2 | 5/2012 | Hammond | |
| 8,224,481 B2 | 7/2012 | Bylsma et al. | |
| 8,261,941 B2 * | 9/2012 | Woo et al. | 222/52 |
| 8,302,812 B2 | 11/2012 | Reynolds | |
| 8,342,363 B2 | 1/2013 | Carpenter et al. | |
| 8,357,114 B2 | 1/2013 | Poutiatine et al. | |
| 8,360,273 B2 | 1/2013 | Reinsel et al. | |
| 8,381,951 B2 | 2/2013 | Helf et al. | |
| 8,389,966 B2 * | 3/2013 | Saiki | 250/574 |
| 8,430,337 B2 | 4/2013 | Pearce et al. | |
| 2002/0020756 A1 | 2/2002 | Yahav | |
| 2003/0079744 A1 | 5/2003 | Bonney et al. | |
| 2003/0132254 A1 | 7/2003 | Giangreco | |
| 2004/0011885 A1 | 1/2004 | McLisky | |
| 2004/0028551 A1 | 2/2004 | Kvietok et al. | |
| 2004/0031274 A1 * | 2/2004 | Cho et al. | 62/126 |
| 2004/0033171 A1 | 2/2004 | Kvietok et al. | |
| 2004/0035949 A1 | 2/2004 | Elkins et al. | |
| 2004/0074935 A1 | 4/2004 | Chon | |
| 2004/0155056 A1 | 8/2004 | Yahav | |
| 2004/0219863 A1 | 11/2004 | Willacy | |
| 2004/0265164 A1 | 12/2004 | Woo et al. | |
| 2005/0004714 A1 | 1/2005 | Chen | |
| 2005/0224596 A1 | 10/2005 | Panopoulos | |
| 2005/0234402 A1 | 10/2005 | Collins et al. | |
| 2006/0011737 A1 | 1/2006 | Amenos et al. | |
| 2006/0037532 A1 | 2/2006 | Eidson | |
| 2006/0060615 A1 | 3/2006 | McLisky | |
| 2006/0078460 A1 | 4/2006 | Ryu et al. | |
| 2006/0086824 A1 | 4/2006 | Pearce et al. | |
| 2006/0137619 A1 | 6/2006 | Dodman et al. | |
| 2006/0153733 A1 | 7/2006 | Sassoon | |
| 2006/0175357 A1 | 8/2006 | Hammond | |
| 2006/0191955 A1 | 8/2006 | McLisky | |
| 2006/0249531 A1 * | 11/2006 | Litchfield | 222/52 |
| 2007/0036673 A1 | 2/2007 | Selander | |
| 2007/0138326 A1 | 6/2007 | Hu | |
| 2007/0204511 A1 | 9/2007 | Lee et al. | |
| 2007/0235555 A1 | 10/2007 | Helf et al. | |
| 2008/0272148 A1 | 11/2008 | Malik et al. | |
| 2008/0277411 A1 | 11/2008 | Beland et al. | |
| 2008/0279731 A1 | 11/2008 | Goreham et al. | |
| 2008/0290113 A1 | 11/2008 | Helf et al. | |
| 2009/0020560 A1 | 1/2009 | Kraus | |
| 2009/0045219 A1 | 2/2009 | Helf et al. | |
| 2009/0045220 A1 | 2/2009 | Helf et al. | |
| 2009/0117012 A1 | 5/2009 | Bankers et al. | |
| 2009/0185951 A1 | 7/2009 | Litten-Brown et al. | |
| 2009/0218413 A1 | 9/2009 | Withers | |
| 2009/0284361 A1 * | 11/2009 | Boddie et al. | 340/439 |
| 2009/0294471 A1 | 12/2009 | Paige | |
| 2009/0302056 A1 | 12/2009 | Butler | |
| 2009/0314849 A1 | 12/2009 | Litten-Brown et al. | |
| 2010/0025427 A1 | 2/2010 | Chiou et al. | |
| 2010/0037512 A1 | 2/2010 | Durand | |
| 2010/0038379 A1 | 2/2010 | Butler et al. | |
| 2010/0044468 A1 | 2/2010 | Granger et al. | |
| 2010/0059602 A1 | 3/2010 | Chiou et al. | |
| 2010/0221143 A1 | 9/2010 | Broncano Atencia et al. | |
| 2010/0226818 A1 | 9/2010 | Miyagi et al. | |
| 2010/0237108 A1 | 9/2010 | Anderson et al. | |
| 2010/0252574 A1 | 10/2010 | Busin | |
| 2010/0266266 A1 | 10/2010 | Garcia Fabrega et al. | |
| 2010/0272599 A1 | 10/2010 | Broncano Atencia et al. | |
| 2010/0320239 A1 | 12/2010 | Sordo et al. | |
| 2011/0030681 A1 | 2/2011 | De Vries et al. | |
| 2011/0073675 A1 | 3/2011 | Wolosuk | |
| 2011/0076185 A1 | 3/2011 | Hammond et al. | |
| 2011/0089260 A1 | 4/2011 | Van Roemburg | |
| 2011/0095044 A1 | 4/2011 | Sipinski | |
| 2011/0125318 A1 | 5/2011 | Dunn | |
| 2011/0200488 A1 | 8/2011 | Cennini et al. | |
| 2011/0278322 A1 | 11/2011 | Reynolds et al. | |
| 2012/0091209 A1 | 4/2012 | Hotaling et al. | |
| 2012/0111884 A1 * | 5/2012 | Choi | 222/52 |

FOREIGN PATENT DOCUMENTS

| | | |
|---|---|---|
| AU | 659805 | 4/1992 |
| AU | 4932300 | 11/2000 |
| AU | 752399 | 7/2001 |
| DE | 19803696 | 8/1999 |
| DE | 10392689 | 4/2005 |
| DE | 10392794 | 6/2005 |
| EP | 038598 | 10/1981 |
| EP | 0274785 | 8/1990 |
| EP | 401060 | 12/1990 |
| EP | 0641727 | 8/1995 |
| EP | 676133 | 10/1995 |
| EP | 0719234 | 7/1996 |
| EP | 757006 | 2/1997 |
| EP | 0956868 | 11/1999 |
| EP | 1194351 | 4/2000 |
| EP | 1076014 | 2/2001 |
| EP | 1184083 | 3/2002 |
| EP | 1214105 | 6/2002 |
| EP | 1214949 | 6/2002 |
| EP | 1240480 | 9/2002 |
| EP | 1316514 | 6/2003 |
| EP | 1370304 | 12/2003 |
| EP | 1382399 | 1/2004 |
| EP | 1407790 | 4/2004 |
| EP | 1430958 | 6/2004 |
| EP | 1522506 | 4/2005 |
| EP | 1547505 | 6/2005 |
| EP | 1645294 | 4/2006 |
| EP | 1675657 | 7/2006 |
| EP | 1695720 | 8/2006 |
| EP | 1726315 | 11/2006 |
| EP | 1771358 | 4/2007 |
| EP | 1824760 | 8/2007 |
| EP | 1844795 | 10/2007 |
| EP | 1848649 | 10/2007 |
| EP | 1848650 | 10/2007 |
| EP | 1874657 | 1/2008 |
| EP | 1976775 | 10/2008 |
| EP | 2041000 | 4/2009 |
| EP | 2111875 A1 | 10/2009 |
| EP | 2143575 | 1/2010 |
| EP | 2187977 | 5/2010 |
| EP | 2190489 | 6/2010 |
| EP | 2200751 | 6/2010 |
| EP | 2204092 | 7/2010 |
| EP | 2207734 | 7/2010 |
| FR | 2671294 | 1/1991 |
| GB | 1033025 | 6/1966 |
| GB | 2054115 | 2/1981 |
| GB | 2094407 | 9/1982 |
| GB | 2248888 | 4/1992 |
| GB | 2305261 | 4/1997 |
| GB | 2085750 | 10/1999 |
| GB | 2375710 | 11/2002 |
| GB | 2392438 | 3/2004 |
| GB | 2392439 | 3/2004 |
| GB | 2392440 | 3/2004 |
| JP | 62171766 | 7/1987 |
| JP | 3114467 | 5/1991 |
| JP | 3159652 | 7/1991 |
| JP | 06170286 | 6/1994 |
| JP | 10085313 | 4/1998 |
| JP | 200070797 | 3/2000 |
| JP | 2002-113398 | 4/2002 |

(56) References Cited

FOREIGN PATENT DOCUMENTS

| | | |
|---|---|---|
| JP | 2004-331517 | 11/2004 |
| JP | 2006-159071 * | 6/2006 |
| JP | 2007-246528 | 9/2007 |
| KR | 10-0284158 | 9/2000 |
| WO | 8805758 | 8/1988 |
| WO | 91/15409 | 10/1991 |
| WO | 9519304 | 7/1995 |
| WO | 9529106 | 11/1995 |
| WO | 9603218 | 2/1996 |
| WO | 9630726 | 10/1996 |
| WO | 9846280 | 10/1998 |
| WO | 9934266 | 7/1999 |
| WO | 0047335 | 8/2000 |
| WO | 00/64802 | 11/2000 |
| WO | 0064498 | 11/2000 |
| WO | 0075046 | 12/2000 |
| WO | 0078467 | 12/2000 |
| WO | 0107703 | 2/2001 |
| WO | 0121226 | 3/2001 |
| WO | 0125730 | 4/2001 |
| WO | 0126448 | 4/2001 |
| WO | 0166157 | 9/2001 |
| WO | 0240177 | 5/2002 |
| WO | 0240376 | 5/2002 |
| WO | 02072161 | 9/2002 |
| WO | 02079679 | 10/2002 |
| WO | 02087976 | 11/2002 |
| WO | 02094014 | 11/2002 |
| WO | 03005873 | 1/2003 |
| WO | 03037748 | 5/2003 |
| WO | 03037750 | 5/2003 |
| WO | 03042068 | 5/2003 |
| WO | 03062094 | 7/2003 |
| WO | 03062095 | 7/2003 |
| WO | 03068412 | 8/2003 |
| WO | 03068413 | 8/2003 |
| WO | 03086902 | 10/2003 |
| WO | 03086947 | 10/2003 |
| WO | 03098971 | 11/2003 |
| WO | 03099682 | 12/2003 |
| WO | 03104109 | 12/2003 |
| WO | 2004002542 | 1/2004 |
| WO | 2004043502 | 5/2004 |
| WO | 2004067963 | 8/2004 |
| WO | 2004073875 | 9/2004 |
| WO | 2004081303 | 9/2004 |
| WO | 2004093927 | 11/2004 |
| WO | 2004093928 | 11/2004 |
| WO | 2004093929 | 11/2004 |
| WO | 2004105816 | 12/2004 |
| WO | 2004105817 | 12/2004 |
| WO | 2004105818 | 12/2004 |
| WO | 2004110507 | 12/2004 |
| WO | 2005001212 | 1/2005 |
| WO | 2005014060 | 2/2005 |
| WO | 2005018691 | 3/2005 |
| WO | 2005023679 | 3/2005 |
| WO | 2005072059 | 8/2005 |
| WO | 2005072522 | 8/2005 |
| WO | 2005113420 | 12/2005 |
| WO | 2006012248 | 2/2006 |
| WO | 2006044416 | 4/2006 |
| WO | 2006058433 | 6/2006 |
| WO | 2006064187 | 6/2006 |
| WO | 2006084317 | 8/2006 |
| WO | 2006104993 | 10/2006 |
| WO | 2006105652 | 10/2006 |
| WO | 2006108043 | 10/2006 |
| WO | 2006114532 | 11/2006 |
| WO | 2007029044 | 3/2007 |
| WO | 2007045828 | 4/2007 |
| WO | 2007045834 | 4/2007 |
| WO | 2007045835 | 4/2007 |
| WO | 2007052016 | 5/2007 |
| WO | 2007064188 | 6/2007 |
| WO | 2007064189 | 6/2007 |
| WO | 2007064197 | 6/2007 |
| WO | 2007064199 | 6/2007 |
| WO | 2007132140 | 11/2007 |
| WO | 2007146332 | 12/2007 |
| WO | 2008056131 | 5/2008 |
| WO | 2008149065 | 12/2008 |
| WO | 2009103738 | 8/2009 |
| WO | 2009130927 | 10/2009 |
| WO | 2009151213 | 12/2009 |
| WO | 2010030629 | 3/2010 |
| WO | 2010039621 | 4/2010 |
| WO | 2010101455 | 9/2010 |
| WO | 2010130891 | 11/2010 |
| WO | 2010145038 | 12/2010 |
| WO | 2011045620 | 4/2011 |
| WO | WO2012/057834 A2 | 5/2012 |
| WO | WO2013/043696 A2 | 3/2013 |

OTHER PUBLICATIONS

PCT/US2013/063005 International Search Report and Written Opinion dated May 22, 2014.

\* cited by examiner

| | | Color of Shroud in Dispensing System | | | | | | | | | |
|---|---|---|---|---|---|---|---|---|---|---|---|
| | | No Shroud | Green Blue | Red | White Speckle | Sandy Stone | Sky Blue | Yellow Speckle | Lime Green | Green Purple | Mustard Yellow | Black Granite |
| 1 | | 13 | 14 | 15 | 15 | 15 | 15 | 16 | 17 | 16 | 17 | 18 |
| 2 | | 13 | 15 | 15 | 16 | 16 | 15 | 16 | 15 | 16 | 17 | 18 |
| 3 | | 13 | 14 | 14 | 15 | 15 | 15 | 16 | 16 | 16 | 16 | 19 |
| 4 | | 13 | 15 | 15 | 15 | 15 | 15 | 15 | 15 | 16 | 17 | 19 |
| 5 | | 13 | 15 | 15 | 15 | 15 | 16 | 15 | 16 | 16 | 17 | 19 |
| Average | | 13 | 14.6 | 14.8 | 15.2 | 15.2 | 15.2 | 15.6 | 15.8 | 16 | 16.8 | 18.6 |
| Improvement Over Baseline (%) | | 0.0% | 12.3% | 13.8% | 16.9% | 16.9% | 16.9% | 20.0% | 21.5% | 23.1% | 29.2% | 43.1% |

FIG. 19

| Data Normalized for Color Impact | | | | | | | | | |
|---|---|---|---|---|---|---|---|---|---|
| Green Blue | Red | White Speckle | Sandy Stone | Sky Blue | Yellow Speckle | Lime Green | Purple | Mustard Yellow | Black Granite |
| 0.0% | 1.5% | 4.6% | 4.6% | 4.6% | 7.7% | 9.2% | 10.8% | 16.9% | 30.8% |

US 9,108,782 B2

DISPENSING SYSTEMS WITH IMPROVED SENSING CAPABILITIES

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present disclosure relates to dispensing systems having improved sensing capabilities.

2. Description of the Background

Diffusion devices or dispensers are used to dispense volatile materials, such as fragrances, deodorants, insecticides, insect repellants, and the like from one or more containers. Many of these dispensers are active dispensers, which may include fans and/or heaters to aid in the dispersal of volatile materials. Other dispensers actuate a valve stem of an aerosol container to dispense a volatile material contained therein, or utilize an ultrasonic transducer to break up a liquid volatile material into droplets that are ejected from the dispenser. Yet other dispensers include any combination of the above or any other known type of active diffusion device.

Traditionally, these active dispensers are standalone devices that release product into a space in response to manual input, a lapsing of a timed interval, or sensory input, e.g., spraying an air freshener within a room or a pest control device within a barn. These dispensers are generally kept "out of sight" of users by placing them in areas of a room or space that are utilized less frequently by users or that provide the ability to "hide" or otherwise diminish the impact of the dispenser on the room or space in which it is located. In these circumstances, the placement of the dispensers in sub-optimal areas of a room or space causes the dispensers to be less effectual in terms of their ability to effectively disperse a volatile material into the room or space.

Further, many of these prior art dispensers utilize sensors to initiate various pre-programmed or user initiated operational sequences, as well as to provide instant dispensing upon the detection of sensory input. In these prior art dispensers a sensor with a single sensing capability, e.g., sensing whether a level of light is diminished within a certain period of time over a certain distance that is indicative of motion, is used regardless of whether the dispenser is placed in a bathroom or an auditorium. As such, the sensors may not always efficiently sense the presence of people in the desired space. For example, if a dispenser with a sensor having the capability of detecting input at a distance of 20 ft is placed in a typical in-home bathroom, the dispenser may incorrectly detect the presence of a user passing the dispenser outside of the bathroom, which may result in an inadvertent activation of the dispenser. Conversely, if a dispenser utilizing a sensor with a sensing range of 5 ft is used in a large room, the sensor may not effectively detect the presence of a user in the room, unless the user happened to pass in close proximity to the dispenser. Accordingly, these prior art dispensers do not include sensors that are efficiently and/or optimally responsive to the environment in which they are located or according to user preferences.

Presently there is a need for dispensers that are intended to be left in "plain view" of a user and otherwise positioned prominently within a room or space, i.e., not hidden or otherwise intentionally obstructed. Further, there is a need for dispensing systems that include efficient sensors, which provide for improved sensing capabilities. Additionally, the sensing systems should be efficient and in some cases capable of being adjusted in response to the space they are located in and according to user preferences. As such, it is an object of the present disclosure to address the disadvantages of the prior art and to fulfill this unmet need.

SUMMARY OF THE INVENTION

According to one embodiment, a dispensing system includes a dispenser, at least one sensor, and a shroud including at least one aperture. A virtual shield is provided between the sensor and the shroud to reduce background noise.

According to another embodiment, a dispensing system includes a dispenser having at least one sensor. A shroud includes at least one aperture spaced from the at least one sensor. An aperture performance factor $S_A$ is defined by the ratio $S_A = S_S/S_V$ and $S_A \leq 1$.

According to a different embodiment, a dispensing system includes a dispenser, at least one sensor, and a shroud including at least one aperture. The shroud is light reflective and includes a colorant that provides a reduction in background noise of at least 10% when compared to the omission of the shroud.

Other aspects and advantages will become apparent upon consideration of the following detailed description and the attached drawings, in which like elements are assigned like reference numerals.

BRIEF DESCRIPTION OF THE DRAWINGS

FIGS. 19-21 are charts that illustrate the results obtained from the test shown in FIG. 18;

DETAILED DESCRIPTION OF THE DRAWINGS

Figure 1:
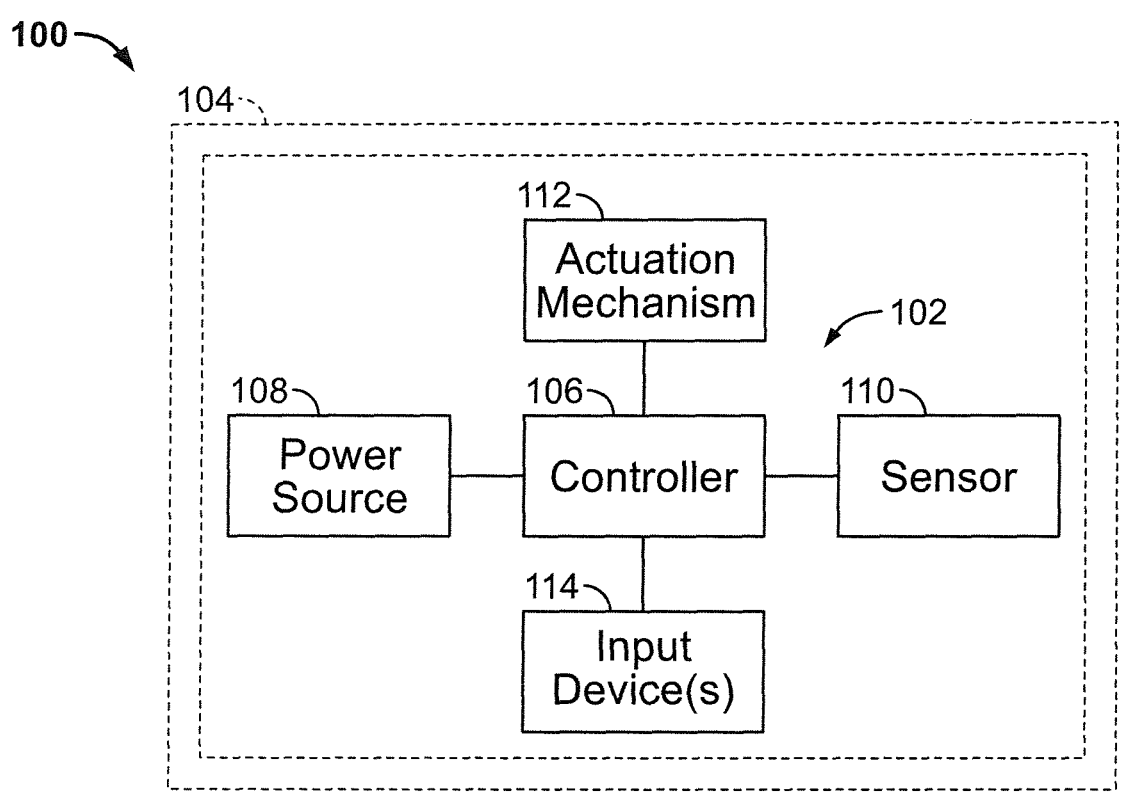
FIG. 1 is a schematic representation of a dispensing system.

FIG. 1 generally depicts a dispensing system 100. The dispensing system 100 includes a dispenser 102 disposed within a shroud or housing 104. The dispenser 102 includes a controller 106, a power source 108, one or more sensors 110, and an actuation or dispensing mechanism 112. The dispenser 102 may also include one or more input devices 114 such as switches, dials, keypads, pushbuttons, etc. An example of an input device 114 may be a switch, which allows the user to turn on the dispenser 102 and/or a pushbutton, which allows the user to initiate a dispense mode to release product from one or more containers 120 (see FIGS. 2A-2D). The power source 108 supplies power to the controller 106 and to other components. The controller 106 is further coupled to the other components and executes programming to control the operation thereof. The power source 108 may include one or more plugs for insertion into a conventional electrical outlet or a corded plug. Additionally, or alternatively, the power source 108 may be an internal power source such as one or more batteries.

The dispenser 102 is configured to discharge product from one or more containers upon the occurrence of a particular condition. The condition could be the manual activation of the dispenser or the automatic activation of the dispenser 102 in response to an elapsed time interval or signal from the sensor 110. The product may include a fragrance, deodorizer, insecticide, insect repellent, or other product, product formulation, or volatile material. For example, the fluid may comprise OUST®, an air and carpet sanitizer for household, commercial, and institutional use, or GLADE®, a household deodorant, both sold by S. C. Johnson and Son, Inc., of Racine, Wis. The fluid may also comprise other actives, such as sanitizers, air and/or fabric fresheners, cleaners, odor eliminators, mold or mildew inhibitors, insect repellents, and the like, or that have aroma-therapeutic properties. The dispenser 102 is therefore adapted to dispense any number of different products. In embodiments that utilize more than one container, the fluid or product within the containers may be the same, similar, or different.

The sensor 110 in the present embodiment may be a photocell light sensor or phototransistor. In one embodiment, changes in the detected level of light by the sensor may be construed as detected motion. The sensor may be the sensor described in Carpenter et al. U.S. patent application Ser. No. 11/725,402. However, any other type of detector or sensor may be utilized for detecting sensory input, e.g., a passive infrared or pyroelectric motion sensor, an infrared reflective motion sensor, an ultrasonic motion sensor, or a radar or microwave radio motion sensor. In some embodiments more than one sensor 110 may be used. It is anticipated that utilization of the sensor 110 (or multiple sensors) will allow for the detection of sensory input, which may be utilized to provide one or more of the powering on or off of the system, the initiation of a pre-programmed timed sequence of dispensing, the initiation of a sequence that comprises one or more dispensing periods between one or more non-dispensing periods, the initiation of a sequence that includes a continual dispensing sequence, the initiation of an immediate dispensing of a product, the initiation of the dispensing of a product after a specified or non-specified delay, the initiation of a dispensing sequence characterized by dispensing a product in response to one or more of a timed interval, sensory input, or manual actuation after the initial detection of sensory input, and the initiation of one or more previously noted actions in connection with a system having a single container, two containers, three containers, or any other number of additional containers 120.

Figure 2A:
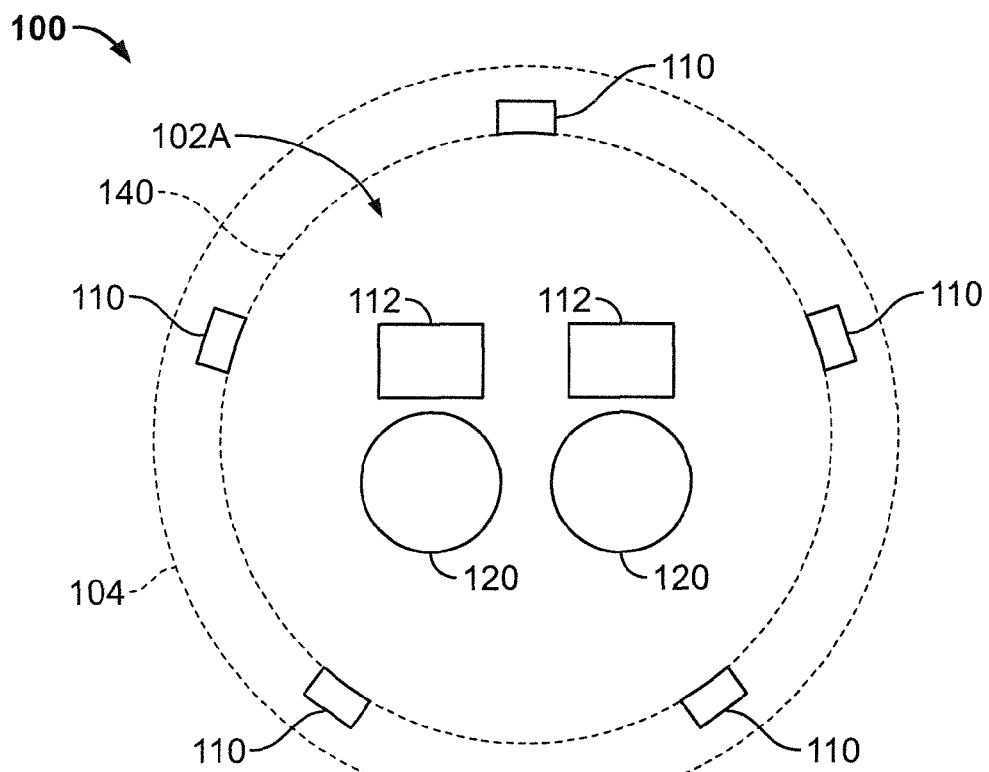
FIGS. 2A-D are schematic representations of the dispensing system of FIG. 1 utilizing various dispensers.

FIGS. 2A-D illustrate various embodiments of dispensers for use in the dispensing system 100. Referring now to FIG. 2A, in one embodiment the dispenser 102A is a conventional electronic dispenser that utilizes one or more actuation mechanisms 112 to spray product from a container 120 such as an aerosol container, whether metered or non-metered, and pump-type sprayers, whether pre-compression or non pre-compression pump-type sprayers. Conventional actuation mechanisms may include, but are not limited to, mechanically driven means, such as armatures, levers, linkages, cams, etc., that depress, tilt, or otherwise activate a valve stem or pump of a container by direct interaction with the valve stem or pump, through indirect communication with the valve stem or pump, and/or through physical interaction with the container, i.e., lifting, pushing, tilting, lowering, or otherwise deflecting the container to effect the depression or tilting of the valve stem or pump. It is also contemplated that solenoid actuators, bi-metallic actuators, muscle wire actuators, piezo actuators, or any other means may be utilized to effect spraying of an aerosol or pump-type container. Further, it is also contemplated that other dispensing and actuation mechanisms 112 may be utilized, such as those used in connection with nebulizers or venturi sprayers. Still further, the dispenser 102A may include a second actuation mechanism 112 to dispense product from a second container 120. The dispenser 102A may utilize a product or fluid provided within a container or reservoir 120 that is pressurized or non-pressurized. The sensor 110 is disposed about a perimeter of a housing 140 of the dispenser 102A to provide a sensory field of view. In one embodiment two sensors are provided, in a different embodiment three sensors are provided, in yet a different embodiment four sensors are provided, in still a further embodiment five sensors are provided. It is contemplated that any number of sensors 110 may be used with the dispenser 102A.

Figure 2B:
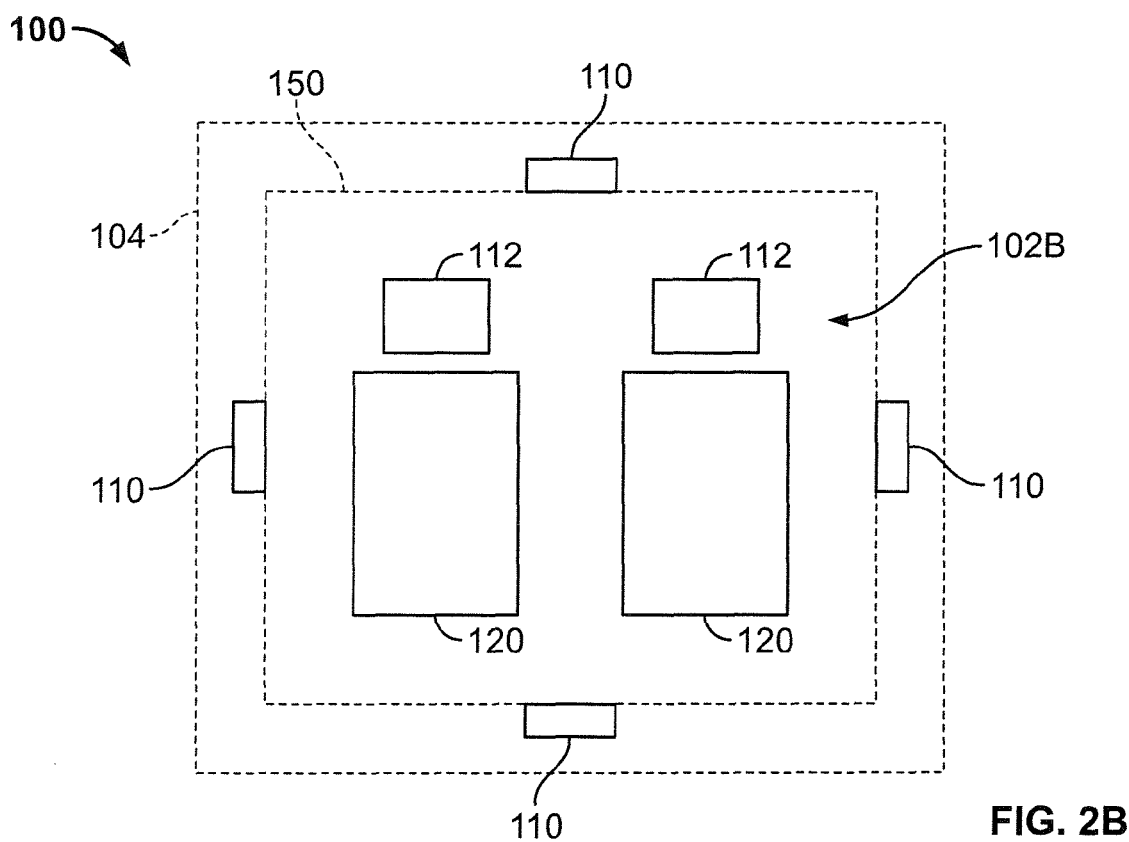

In a different embodiment illustrated in FIG. 2B, the illustrated dispenser 102B is a conventional oil or product diffuser. It is contemplated that the dispensing or diffusing of a product from the container 120 may be realized by one or more dispensing mechanisms 112 such as activation means that include heating a container, heating a wick extending from or into the container, heating an area adjacent a wick and/or container, running a fan adjacent an aperture of a container or a wick extending from a container, running a fan within a housing to assist in dispersal of a product, activating a piezo-electric plate adjacent a wick to volatize a fluid thereon, opening a window or otherwise removing an obstruction from an aperture to assist in the dispersal or diffusion of product from the dispenser 102B, or any other known means for diffusing. Further, the dispenser 102B may be adapted to include a second activation means 112 to dispense or diffuse product from a second container or reservoir 120. The sensor 110 is disposed about a perimeter of a housing 150 of the dispenser 102B to provide a sensory field of view. In one embodiment two sensors are provided, in a different embodiment three sensors are provided, in yet a different embodiment four sensors are provides, in still a further embodiment five sensors are provided. It is contemplated that any number of sensors 110 may be used with the dispenser 102B.

Figure 2C:
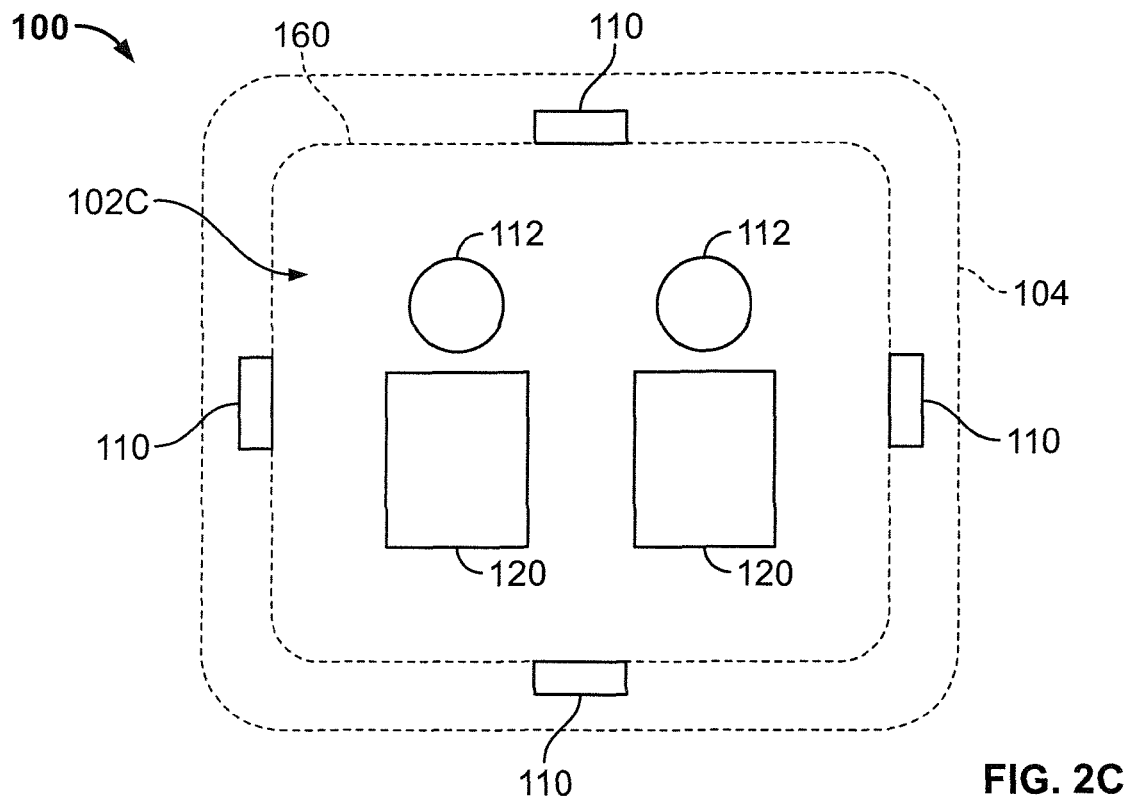

FIG. 2C illustrates a further embodiment of a dispenser 102C that has a dispensing mechanism 112 such as a conventional diffuser that utilizes a cartridge or reservoir 120 that holds one or more of a product, volatile, or active laden gel or liquid. Alternatively, the diffuser 102C may include two cartridges or reservoirs 120, three cartridges or reservoirs, or any number of additional cartridges or reservoirs. It is contemplated that diffusion may be realized by one or more dispensing mechanisms 112 having activation means that provide for one or more of heating a cartridge or reservoir, heating an area adjacent a cartridge or reservoir, running a fan adjacent an aperture or vapor permeable membrane of a cartridge or reservoir, running a fan within a housing to assist in dispersal of a product, rotating or otherwise moving a cartridge or reservoir, opening a window or otherwise removing an obstruction from an aperture or opening to assist in the dispersal of product from the housing, or any other known means of diffusing. The sensor 110 is disposed about a perimeter of a housing 160 of the dispenser 102C to provide a sensory field of view. In one embodiment two sensors are provided, in a different embodiment three sensors are provided, in yet a different embodiment four sensors are provides, in still a further embodiment five sensors are provided. It is contemplated that any number of sensors 110 may be used with the dispenser 102C.

Figure 2D:
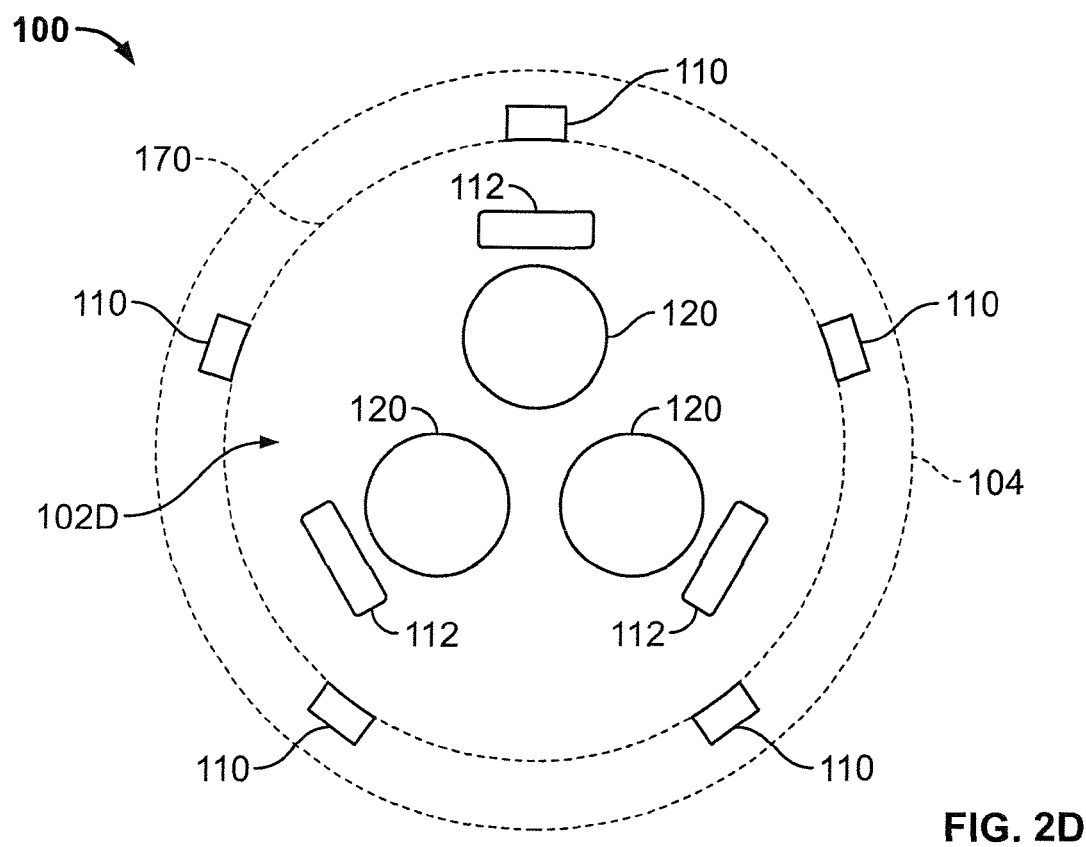

In still another embodiment, shown in FIG. 2D, a dispenser 102D is a system that includes one or more candles, fragrance blocks, wax melts, or products 120, whether solid or gel, that allow for the diffusion of an active or volatile through the melting thereof (hereinafter referred to collectively as "candles"), provided within a housing 170 or on a base. The housing 170 may include one or more candles, e.g., two candles, three candles, four candles, five candles, or any additional number of candles. The sensor 110 is disposed about a perimeter of the housing 170 of the dispenser 102D to provide a sensory field of view. In one embodiment two sensors are provided, in a different embodiment three sensors are provided, in yet a different embodiment four sensors are provides, in still a further embodiment five sensors are provided. It is contemplated that any number of sensors 110 may be used with the dispenser 102D. The one or more sensors 110 allow for the detection of sensory input, which may be utilized to provide the powering on or off of the dispensing mechanism 112, which in the present embodiment comprises one or more heater(s).

Any of the dispensers 102, 102A-D (hereinafter collectively referred to as 102) discussed above may be enclosed within a shroud or housing 104, to create a more aesthetically pleasing dispensing system 100, which a user will leave in "plain view" and otherwise positioned prominently within a room or space, i.e., not hidden or otherwise intentionally obstructed. By placing the dispensing system 100 in plain view, the sensor or sensors 110 (hereinafter individually and collectively referred to as 110) of the dispensing system 100 will be more effective at sensing the presence of persons, objects, or an environmental condition within the space, i.e., the sensing capabilities of the sensor will be improved. The shroud 104 may be constructed from any suitable material, such as plastic, metal, glass, or combinations thereof. Additionally, the materials may include combinations of manufactured, natural, and recycled or reclaimed materials. The shroud 104 may be any shape or any color known to those skilled in the art. In some cases, the materials selected to construct the shroud 104 are configured to approximate naturally occurring substances, such as wood, stone, paper, or rock, or combinations thereof.

Figure 3:
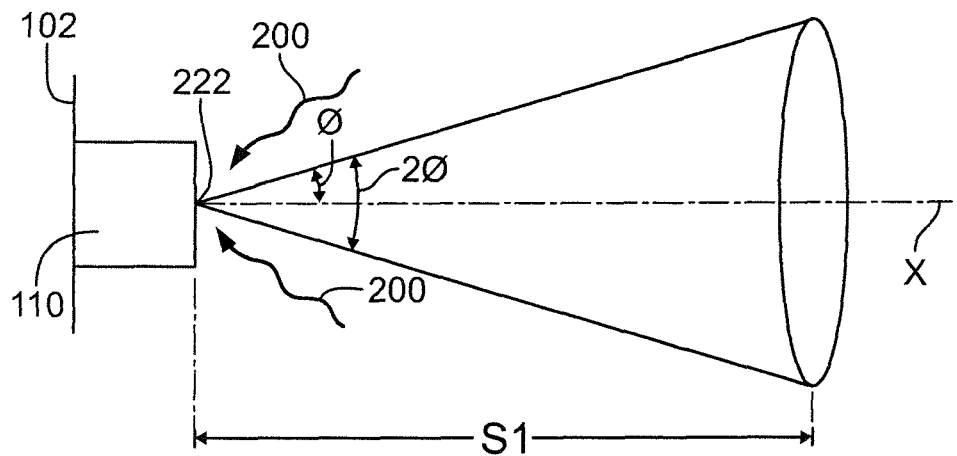
FIG. 3 is a schematic view of a sensor having a field of view.

As shown in FIG. 3, the sensor 110 is disposed on or adjacent to a perimeter of the dispenser 102, or otherwise within the dispenser 102. The sensor 110 has a field of view characterized as a right circular cone having a half angle Ø off a center axis X thereof, which provides for a total viewing angle or sensory field of view of 2Ø. It is contemplated that any sensor that detects light along any portion of the visible or non-visible spectrum may be characterized as having such a viewing angle or sensory field of view. In certain instances, various industry standards or optimal viewing angles will be ascribed to various sensors, which are contemplated to be synonymous with the above noted description. Further, to the extent that such an industry standard does not exist (or that it conforms to the below noted definition), the viewing angle shall be defined as to where the sensitivity drops to 50% of the on axis sensitivity. In one particular non-exclusive embodiment, the sensor 110 is a photodiode that includes a viewing angle Ø of about 10 degrees and a sensory field of view 2Ø of about 20 degrees. The sensitivity of the photodiode drops to 50% of the on X axis sensitivity at about 10 degrees off the X axis. In other embodiments, the sensory field of view 2Ø is between about 10 degrees to about 180 degrees, more preferably between about 10 degrees to about 90 degrees, and most preferably between about 10 degrees to about 45 degrees.

The sensor 110 has the ability to detect sensory input over a distance S1, in which the sensor is effective in detecting the sensory input or a change therein. For example, the sensory input may be a detected level of light or any change therein when utilizing a photodiode. A change in the detected level of light may be dependent on a period of time in which the level of light was collected or independent of any temporal restriction. In one embodiment, a detected change in light intensity within a time period P is indicative of motion, whereas a change in light intensity less than or greater than P is not.

It is understood that either one or more of the sensor(s) 110 or controller 106 may process any sensory input. The intended processing in either the sensor 110 or controller 106 is applicable to all embodiments disclosed herein, regardless of how initially characterized.

The sensing efficiency of the sensor 110 over the sensing distance S1 is dependent on the ratio between the signal strength of the sensory input and any detected background noise 200, i.e., sensory input outside the field of view 2Ø that reaches the sensor 110. In the present embodiment, the background noise 200 would comprise light outside the field of view 2Ø. As the amount of background noise 200 reaching the sensor 110 is reduced, the sensing capabilities of the sensor will improve and the sensor will be able to detect sensory input at a greater sensing distance S1 away from the sensor. In connection with the present embodiment, by decreasing the amount of light reaching the sensor 110 outside of the optimal field of view 2Ø, the sensing capabilities of the sensor 110 will be improved to better detect sensory input, i.e., motion.

Figure 4:
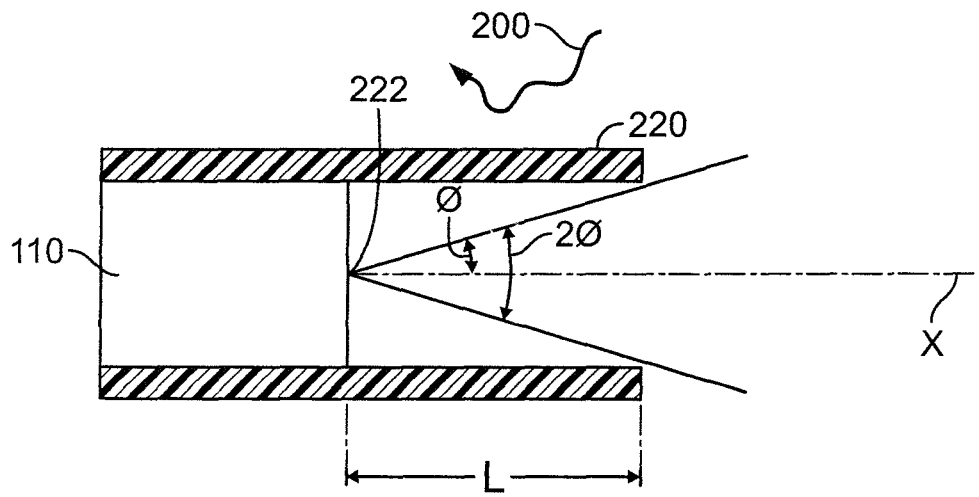
FIG. 4 is a schematic, partial sectional view of a sensor and lens with a field of view.
Figure 4A:
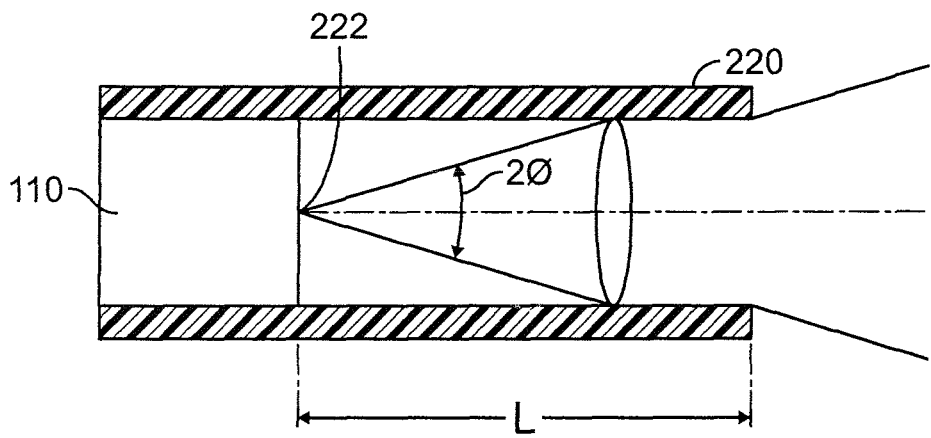
FIG. 4A is an alternative embodiment of the sensor of FIG. 4 with a modified field of view.

Referring to FIG. 4, a lens cover 220 such as a cylindrical tube or housing may be disposed around the sensor 110. In the present embodiment, the lens cover 220 protrudes a distance L from a front focal point 222 of the sensory field of view of the sensor 110. The lens cover 220 operates as a sensory shield to reduce and/or prevent interference with the sensor 110 by reducing and/or preventing background noise 200 from reaching the sensor. Further, with reference to FIG. 4A, an alternative embodiment is shown in which the length L of the lens cover 220 extends beyond the sensor 110 to a point where the sensory field of view is reduced to <2Ø, thereby restricting the field of view of the sensor 110 to alter the sensing capabilities of the sensor.

Figure 5:
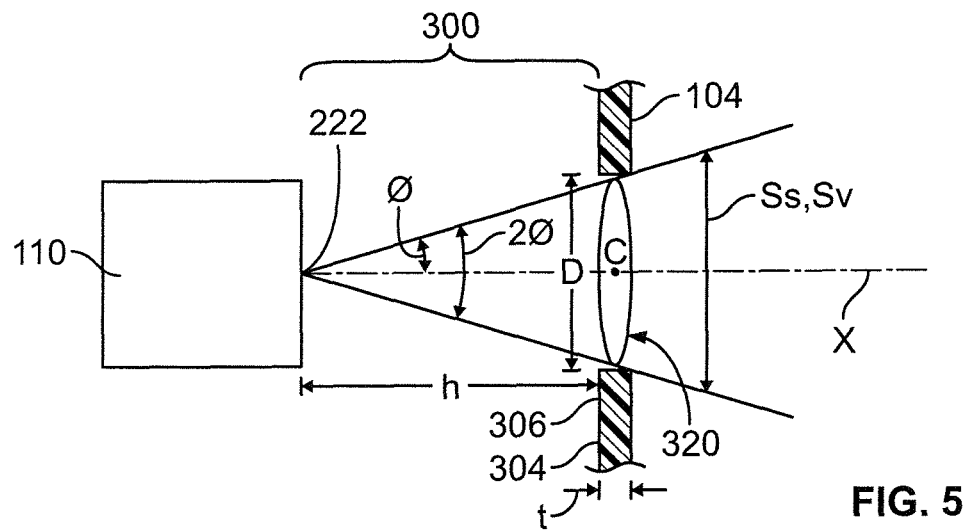
FIG. 5 is a schematic, partial sectional view of a sensor similar to those described in FIGS. 3, 4, and 4A shown with a virtual shield.

Turning to FIG. 5, the sensor 110 depicted in FIGS. 3, 4 (with a lens cover 220), and/or 4A (with a lens cover 220 and restricted view) may be used in conjunction with a shroud or housing 104. The shroud 104 of the present embodiments assists in the creation of a virtual shield 300 between the shroud 104 and the sensor 110 to reduce background noise. More specifically, the virtual shield 300 is provided in a space or gap between a distal or input end, i.e., the focal point 222, of the sensor 110 and an inner side 304 of a sidewall 306 of the shroud 104. With reference to FIG. 5, it may be seen that the inner side 304 of the shroud 104 is coincident with at least one aperture 320. The aperture 320 of the present embodiment is shown as devoid of any material, i.e., an opening, but it is contemplated that the aperture could include a glass, or plastic, or other light transmissive material extending thereacross. Preferably, the central or center axis X of the sensor 110 extends through a portion of the aperture 320. In one preferred embodiment, a center C of the aperture 320 is aligned with the axis X. The virtual shield 300 provides for an increase in the sensing capabilities of the dispenser 102 by filtering out background noise that would otherwise reach the sensor 110. In connection with the present embodiment, background light noise is diminished through use of the virtual shield 300 to increase the sensing capabilities of the sensor 110. Further, placement of the dispenser 102 within the shroud 104 will encourage users to leave the dispensing system 100 in plain sight, thereby increasing the efficiency of the sensor 110 in yet another way.

Referring still to FIG. 5, the dispenser 102 and the sensor 110 are shown disposed adjacent to a shroud 104. While the shroud 104 is illustrated as a partial sectional view of a sidewall, the shroud 104 may comprise any structure that effects some form of reduction in sensory input background noise. In one embodiment, the shroud 104 comprises a discrete wall portion adjacent the sensor 110. In other embodiments, the shroud 104 partially or completely circumscribes the dispenser 102 within the shroud.

The sensor 110 is disposed within the shroud 104 at a distance h measured along the center axis X from the inner side 304 of the shroud 104 to a front focal point 222 of the field of view 2Ø of the sensor 110. Thus, in this embodiment, the virtual shield 300 created by the shroud 104 is equal to the distance h. In the embodiments that utilize lenses such as those shown in FIGS. 4 and 4A, the virtual shield 300 would have a distance of h–L. The aperture 320 is provided in the sidewall 306 of the shroud 104 to allow the sensor 110 to detect sensory input outside of the dispensing system 100. The size of the aperture 320 is preferably large enough to not significantly impede the sensor's 110 field of view while not being too large that excessive background noise is able to reach the sensor. In one embodiment, the aperture 320 is circular in shape and has its center C on the center axis X of the sensor 110. In this embodiment, the preferred diameter D of the aperture 320 is dependent on the distance the sensor 110 is from the aperture and the viewing angle Ø. The equation for determining the diameter D of the aperture is:

$$D = 2(h * \tan \emptyset))$$

By sizing the diameter D of the aperture 320 in this manner, increased efficiencies may be realized within the dispensing system 100 through the elimination of sensory input background noise that would otherwise be received through a wider aperture. In the present embodiment the aperture 320 is a circle that is perpendicular to the center axis X of the sensor 110. However, it is contemplated that the aperture 320 may be any shape and may be oriented at various angles with respect to the center axis X.

The performance of the aperture 320 can be characterized as the amount of background noise that the aperture excludes. Any sensory input that is outside the field of view 2Ø of the sensor 110 is background noise and is reducing the effective performance of the sensor. An aperture performance factor $S_A$ is the ratio of a virtual surface area represented by the intersection of a sensor field of view $S_V$ and a surface area defined by the aperture intersection of the shroud surface $S_S$. As such:

$$S_A = S_S / S_V.$$

If the two surface areas $S_V$ and $S_S$ are coincident, the aperture performance factor $S_A$ equals 1.0 (see FIG. 5). The closer the aperture performance factor $S_A$ is to 1 the more efficient the aperture is because it allows for the entire field of view 2Ø of the sensor 110 to pass through the aperture 320, while limiting the amount of noise reaching the sensor. Thus, an aperture performance factor SA of about 1 provides for optimal sensing capabilities and performance.

Figure 6:
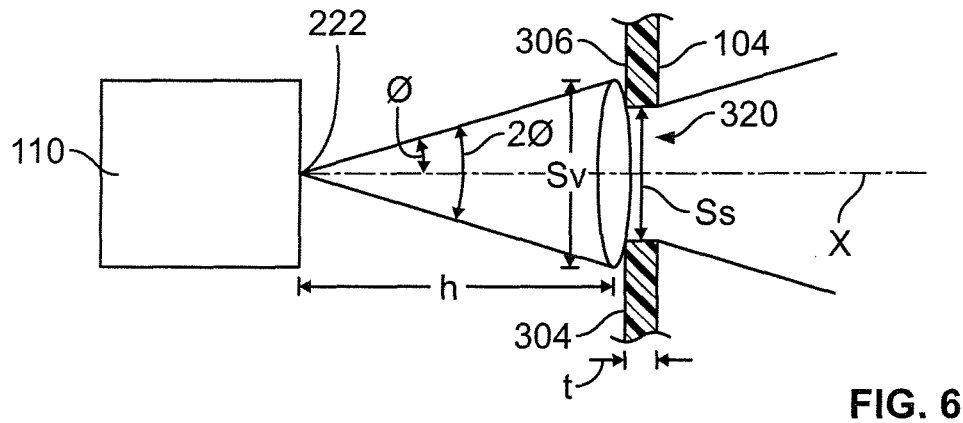
FIGS. 6-17 illustrate schematic, partial sectional views of sensors within the dispensing system of FIG. 1.

Referring now to FIG. 6, the size of the aperture 320 is reduced, such that portions of the sidewall 306 defining the aperture 320 block part of the field of view 2Ø. In this case the surface area $S_V$ of the field of view of the sensor 110 intersecting the housing 104 is larger than the surface area $S_S$ of the aperture 320 intersecting the shroud 104 at the inner side 304 of the sidewall 306. In such cases, the aperture performance factor $S_A$ is less than one. When the aperture 320 is smaller than the field of view 2Ø of the sensor 110, the field of view 2Ø subsumes the aperture such that reduced and/or no background noise passes through the aperture to the dispenser. Further, it is possible to tune the sensing distance S1 of the sensor 110 by decreasing the size of the aperture 320, thereby partially blocking a portion of the field of view 2Ø of the sensor.

Figure 7:
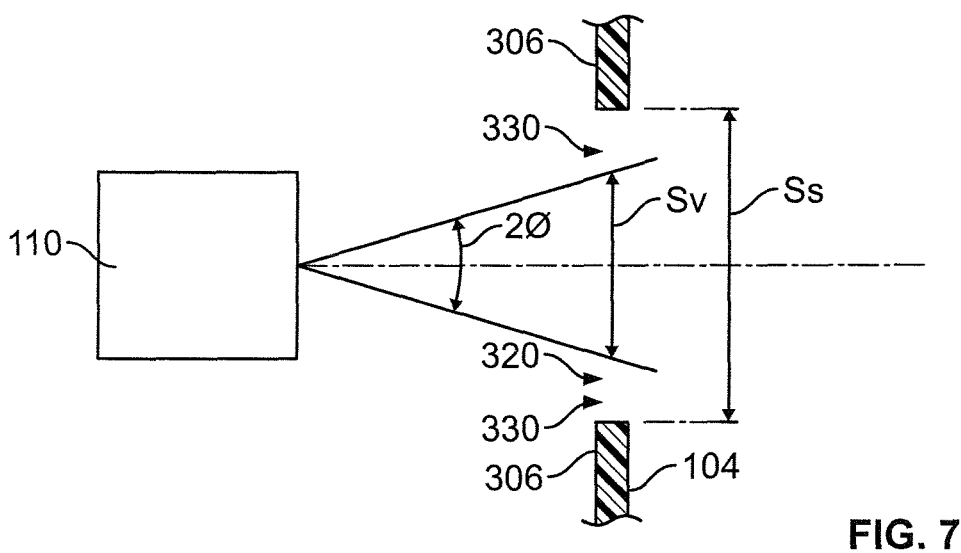

As shown in FIG. 7, in some embodiments the size of the aperture 320 is larger than the field of view 2Ø of the sensor 110 such that gaps 330 exist between the field of view 2Ø of the sensor and the portions of the sidewall 306 defining the aperture 320. In this case, the field of view surface area $S_V$ of the sensor 110 intersecting the shroud 104 is smaller than the surface area $S_S$ of the aperture 320 in the shroud 104, which provides an aperture performance $S_A$ greater than 1. When the aperture performance $S_A$ is greater than 1, the aperture is not properly shielding the sensor 110, i.e., more background noise is reaching the sensor 110, thereby decreasing the performance of the sensor.

Figure 8:
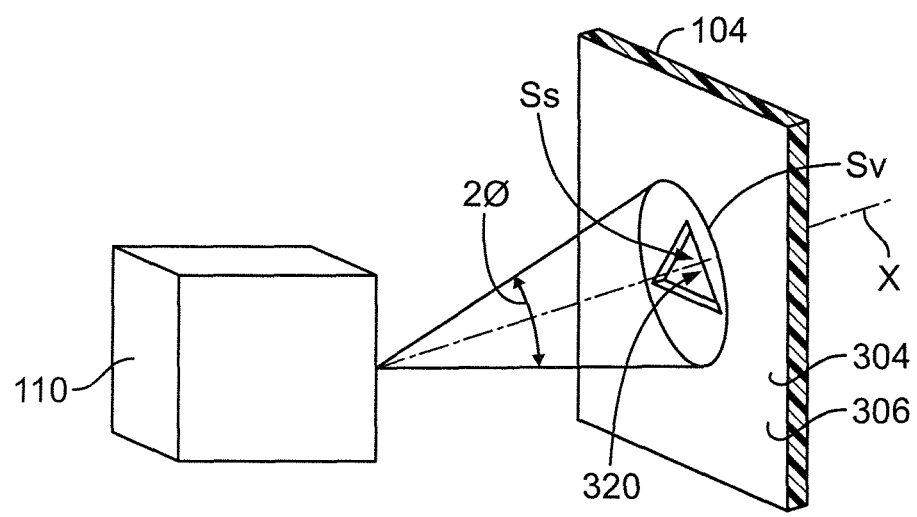

In an alternative embodiment, in which one example is depicted in FIG. 8, the sensor 110 and the aperture 320 have distinctly different shapes. For example, FIG. 8 depicts the aperture 320 as having a triangular cross-section and the field of view 2Ø of the sensor as having a circular cross-section. However, so long as the surface area $S_V$ of the field of view of the sensor 110 completely subsumes the surface area $S_S$ of the aperture 320 in the shroud 104 sidewall, the aperture performance $S_A$ would be optimized to be ≤1. In other embodiments, one or more of the aperture 320 and the field of view 2Ø of the sensor 110 may have any geometric shape, including a square, a rectangle, a circle, an ellipse, an oval, a polygon, a star shape, etc.

Figure 9:
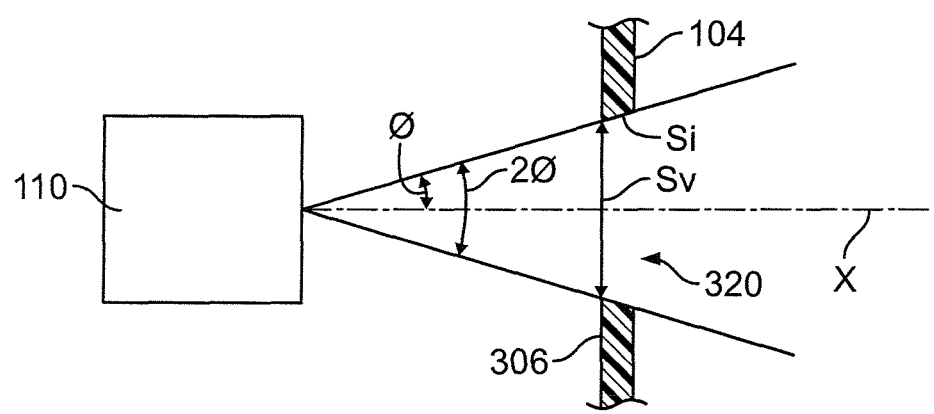
Figure 10:
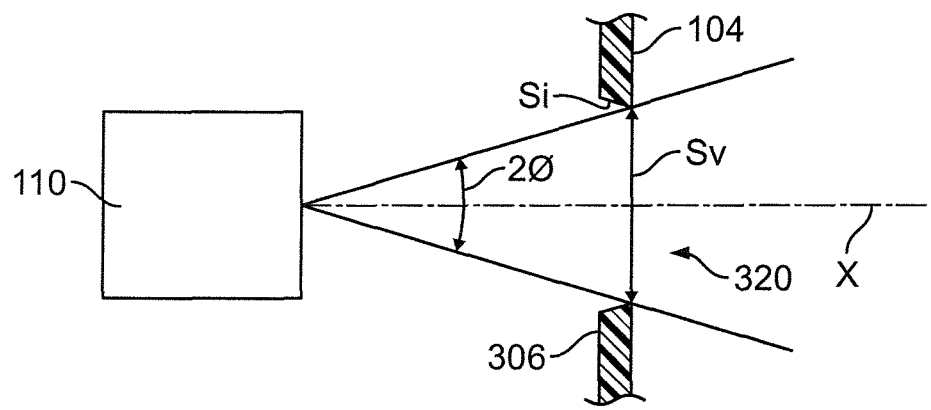

Referring now to FIGS. 9 and 10, it may be seen how the geometry of the aperture 320 cross-section can effect the aperture performance factor $S_A$. Specifically, if an inner surface Si of the aperture 320 is coincident with the surface area $S_V$ defined by the field of view 2Ø of the sensor 110, the aperture performance factor $S_A$ is equal to 1, regardless of where along the inner surface Si the measurement is taken (see FIG. 9). In contrast, if the surface Si is not continually coincident throughout its length with the surface area Sv, then the point at which the $S_V$ first intersects the surface Si must be determined and the aperture performance factor $S_A$ calculated from there (see FIG. 10). In this scenario, the aperture performance factor will be ≤1. It is contemplated that the surface Si of the aperture could have a linear or non-linear shape. However, insofar as the $S_V$ first intersects the inner side 304 of the sidewall 306 or is coextensive with, or intersects with, the surface Si, then the aperture performance factor will be ≤1.

It is contemplated that the portion of the shroud 104 in which the aperture 320 is disposed may be removable from the remainder of the shroud 104 or that the entire shroud may be removable from the dispenser. Preferably, a different shroud portion or shroud 104 may be provided with a differently sized aperture 320 and/or an aperture having a different inner surface Si geometry and/or thickness t. As previously noted, modifying the size of the aperture 320 alters the sensing range S1 of the dispensing system 100.

It is beneficial to be able to adjust the sensing distance S1 of the sensor 110 so that the dispensing system 100 can be optimized for the space in which it is located or according to user preferences. For example, if a dispenser 102 with a sensor 110 having the capability of detecting input at a distance of 20 ft is placed in a typical in-home bathroom, the dispenser may incorrectly detect the presence of a user passing the dispenser 102 outside of the bathroom, which may result in an inadvertent activation of the dispenser. Additionally, the sensing distance S1 can be reduced for dispensing systems 100 located within a vehicle, such that movement outside of the vehicle does not cause the sensor 110 to inadvertently register the sensory input. Conversely, if a dispenser 102 utilizing a sensor 110 with a sensing range of 5 ft is used in a large room, the sensor may not effectively detect the presence of a user in the room, unless the user happened to pass in close proximity to the dispenser. Thus, it is beneficial to adjust the sensing distance S1 according to the space in which the dispensing system 100 is located to most efficiently detect sensory input.

Figure 11:
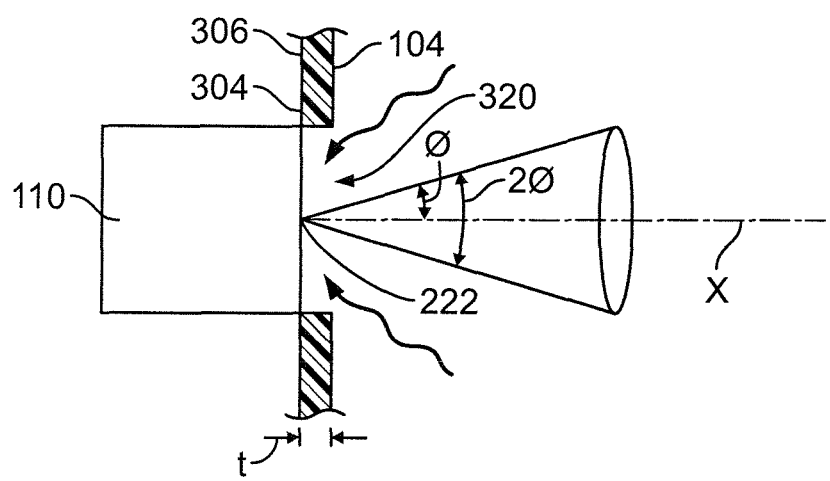

Alternatively, as shown in FIG. 11, if it is desired to reduce the sensing capabilities of the dispenser 102, such that the sensor 110 has a less efficient sensing range or distance S1, the sensor may be located closer to the sidewall 306. In the present embodiment, the sensor 110 is shown as being placed directly adjacent the inner side 304. As the distance h between the sensor and the sidewall decreases, to the point depicted in FIG. 11 where the sensor 110 is directly adjacent the sidewall 306, the amount of background noise reaching the sensor increases, thereby reducing the sensing capabilities of the sensor.

Figure 12:
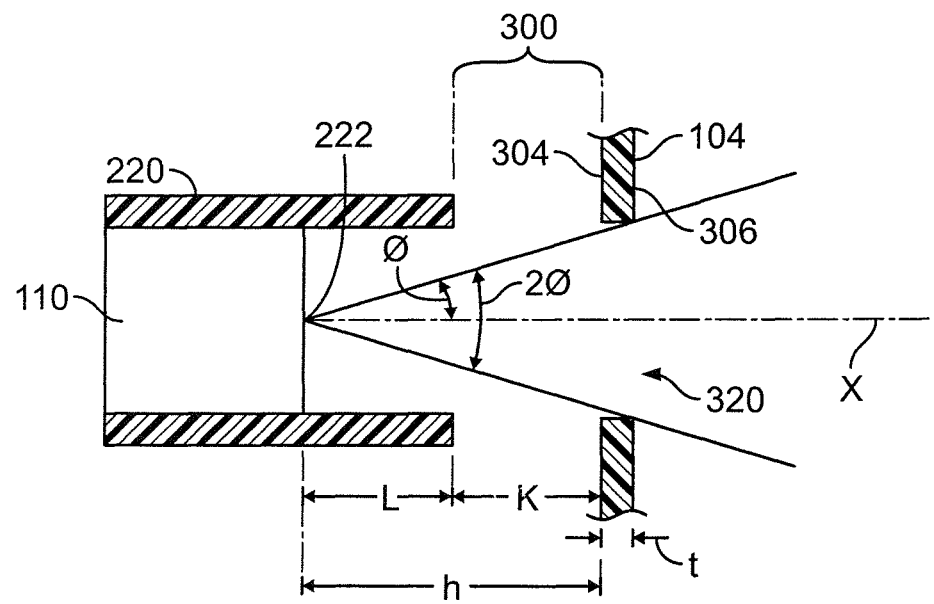

Referring now to FIG. 12, in an alternative embodiment the lens cover 220 is not omitted. Rather, the sensor 110 with the lens cover 220 is disposed within the shroud 104. As discussed above, the lens cover 220 extends a distance L past the front focal point 222 of the field of view 2Ø of the sensor 110. A distal end of the lens cover 220 may be disposed adjacent to the inner side 304 of the sidewall 306 defining the aperture 320, or the distal end of the lens cover 220 may be located a distance K from the inner side 304. As the distance K increases a virtual shield 300 is formed between the distal end of the lens cover 220 and the inner side 304 of the sidewall 306 of the shroud 104.

Figure 13:
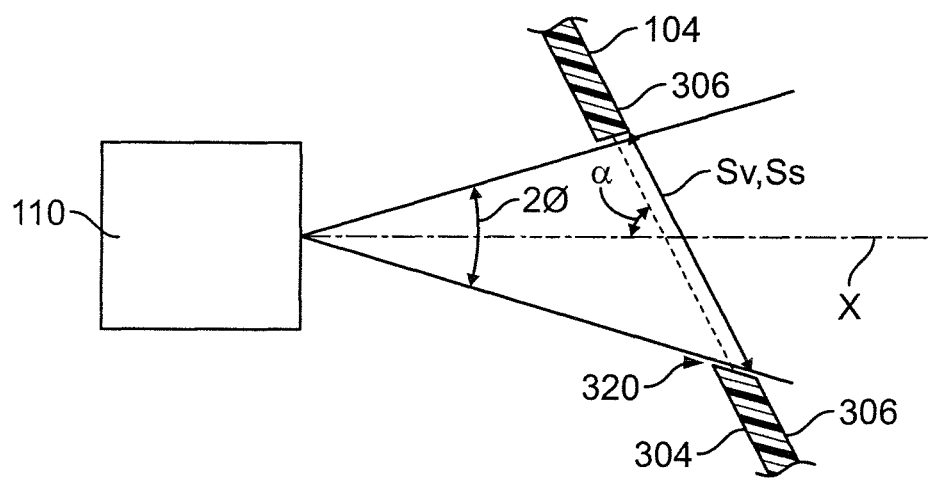

In an alternative embodiment shown in FIG. 13, the sidewall 306 of the shroud 104 is not perpendicular to the center axis X of the sensor 110, but rather is disposed at an angle α from the center axis X. As shown in FIG. 13, when the shroud 104 sidewall 306 is angled the surface area Sv of the field of view 2Ø of the sensor defined by the intersection with the shroud 104 is also disposed at an angle α from the center axis X. Additionally, the surface area Ss of the aperture in the shroud is also disposed at an angle α. So long as the ratio between $S_S$ and $S_V$ is ≤1 the dispensing system will achieve its greatest sensing capabilities.

Figure 14:
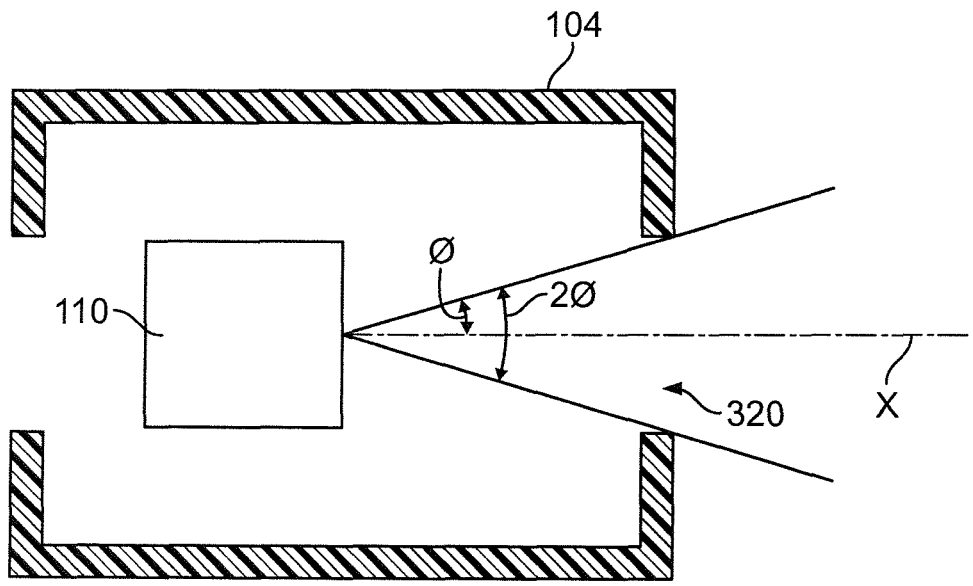
Figure 15:
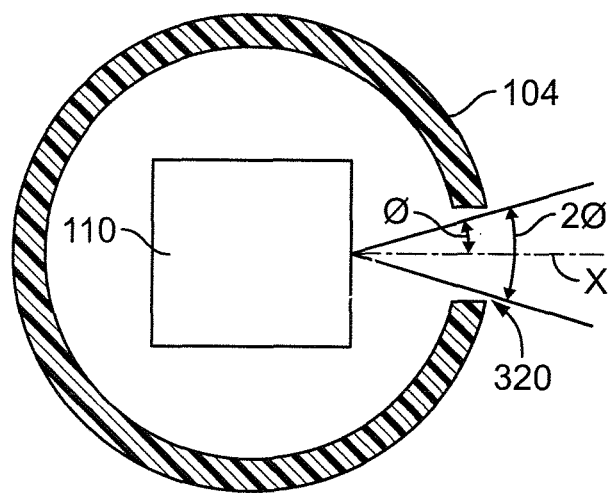
Figure 16:
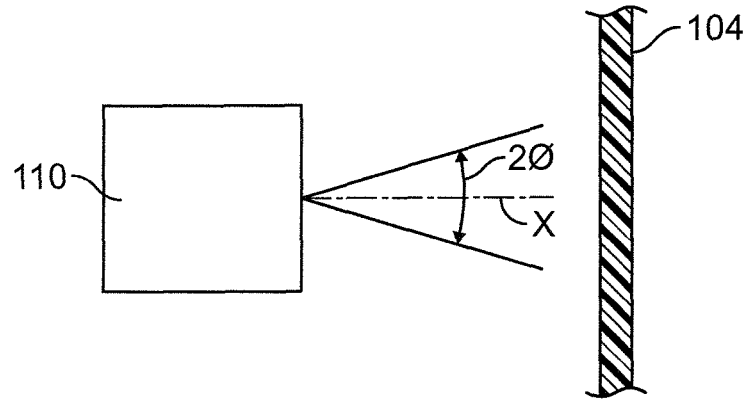
Figure 17:
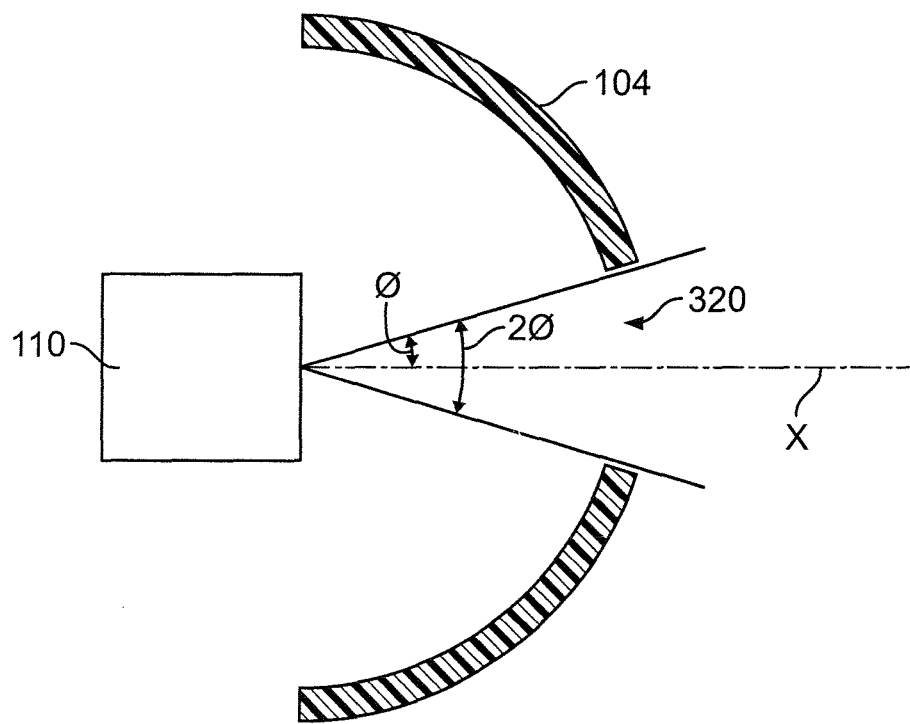

The shroud 104 may comprise any shape capable of enclosing the dispenser 102 therein. However, while it is preferred to provide a shroud 104 that fully, or substantially fully, encapsulates the dispenser 102 (see FIGS. 14 and 15), it is contemplated that variations may be utilized. Indeed, the shroud 104 may be fashioned to only partially cover the dispenser 102, insofar as the shroud 104 still exhibits sensory input noise reduction to the sensor 110. For example, the shroud 104 may comprise a plate that is provided adjacent the sensor 110 (see FIG. 16). Alternatively, the shroud 104 may comprise a curved plate that provides for substantially greater noise reduction and that extends to a point perpendicular to the axis X of the sensor 110 (see FIG. 17).

Additional improvements to the sensing capabilities of the dispensers 102 can be achieved by changing the properties of the shroud 104 itself. While the shroud 104 provides a virtual filtering effect between the aperture 320 and the sensor 110, it was also determined that the material comprising the shroud 104 had a substantial effect on the relative background noise as well. Specifically, it was determined that background noise was reaching the sensor 110 because of the relative reflective nature of the shroud 104 adjacent the aperture 320. Conventional materials used in the manufacturing of the shroud include thermoplastics, such as polyethylenes, polypropylenes, polyesters, etc. While such materials can have significant reflective properties, manufacturing costs and consumer desires typically require that such materials be used to manufacture dispensing systems. With these constraints, the elimination of background noise while still utilizing preferred light reflective materials poses a challenge to effective sensory perception. It has been surprisingly found that certain modifications to colorants used with various shrouds 104 will realize a reduction in background noise and increased sensory effectiveness.

Reflectance is dependent on the surface characteristics, chemical composition, and physical structure of the material. In the present embodiment, the amount of light that is either absorbed by the shroud 104 or that is reflected off of the shroud depends on the chemical composition or microstructure of the material. As such, the dyes used during the molding or manufacture of the shroud 104 will change the chemical composition of the shroud, which will in turn change the relative reflectance properties of the shroud. Thus, the colorant applied to the shroud 104 significantly impacts the sensing capabilities of the dispenser including the sensing distance S1 of the sensor 110.

Figure 18:
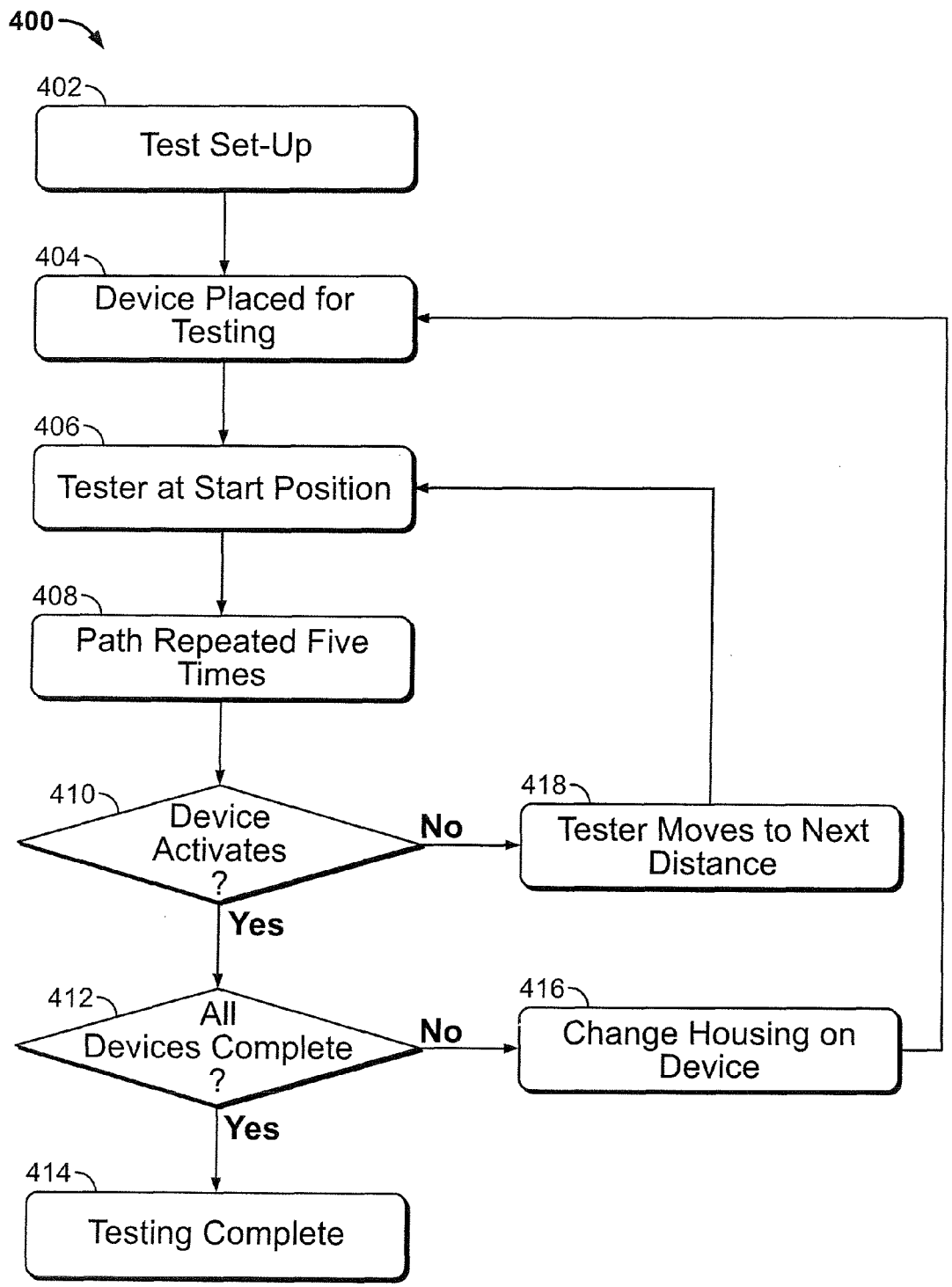
FIG. 18 is a flowchart that illustrates a testing method for determining improvements to the sensing capabilities of a dispensing system.

A test 400, shown in the flow chart of FIG. 18, may be conducted to collect data to determine the improvements to the sensing capabilities of dispensers in relation to the addition of a shroud and the addition of shrouds of various colors. The first step of the test represented as block 402 is the setting up of the test environment. The test is performed in a room having a constant lighting of 380 lux and an uninterrupted target area demarcated by distance lines perpendicular to a center axis X of the sensor and provided at distances of between 12 to 20 feet from the sensor. Preferably, the distance lines are provided every foot, however, the distance lines may be separated by any interval. The room is large enough so that the distance lines may completely traverse the viewing angle 2Ø of the sensor. The first test is run with a conventional prior art dispenser without a shroud to obtain a baseline in sensing characteristics.

The dispenser is then placed within the room (block 404) on a table located at a height of 3 feet above the floor. A tester will then position himself at an end of the distance line the farthest from the dispenser (block 406). Thereafter, the tester walks the length of the distance line and the dispenser is observed to see if the sensor registers any change in light intensity, i.e., movement of the tester. The tester walks the first distance line five times and the observations are recorded (see block 408).

Upon completion of the five observations, a query is undertaken (see block 410) to determine whether the sensor has registered the tester. In the present example, the distance line the tester was walking on when the dispenser sensed the presence of the tester within the viewing angle is recorded as the sensing distance. If registration has occurred at least once, the tester moves to a query block 412 where a determination is made if all of the devices have been tested. If all the devices have been tested, the test 400 is complete (see block 414). If all of the devices have not been tested, the device is removed from the housing and put within a different housing (see block 416) and the new device is tested starting at block 404. The same device is used in each differently colored shroud. If the query undertaken at block 410 results in no registration having occurred, the tester moves to the next distance (see block 418) and starts the procedure at block 406.

Figure 20:
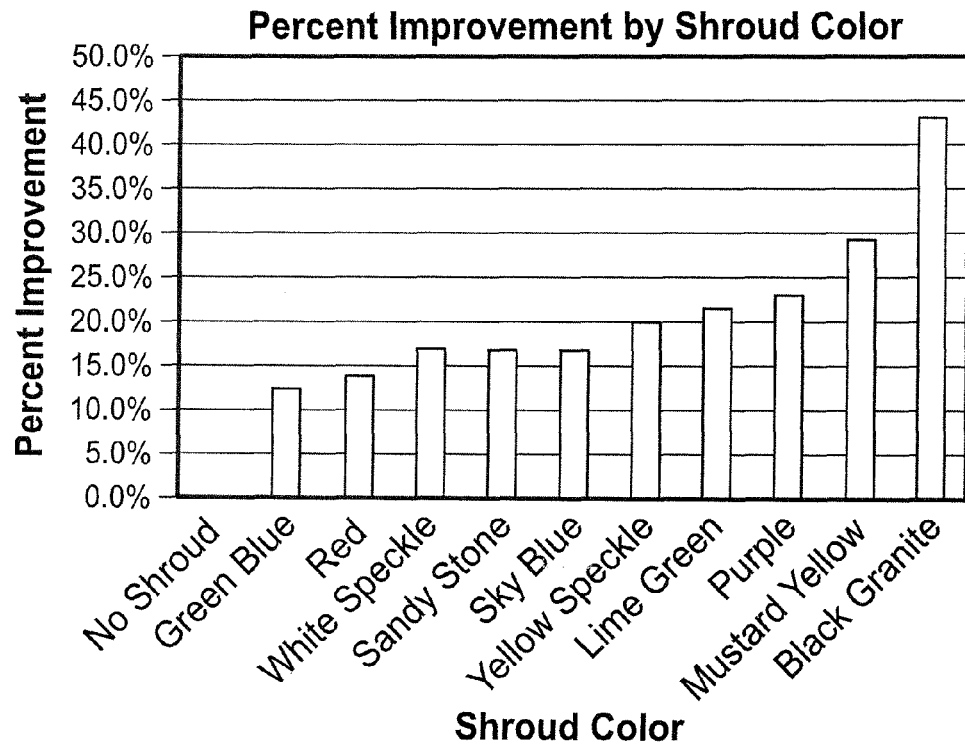
Figure 21:
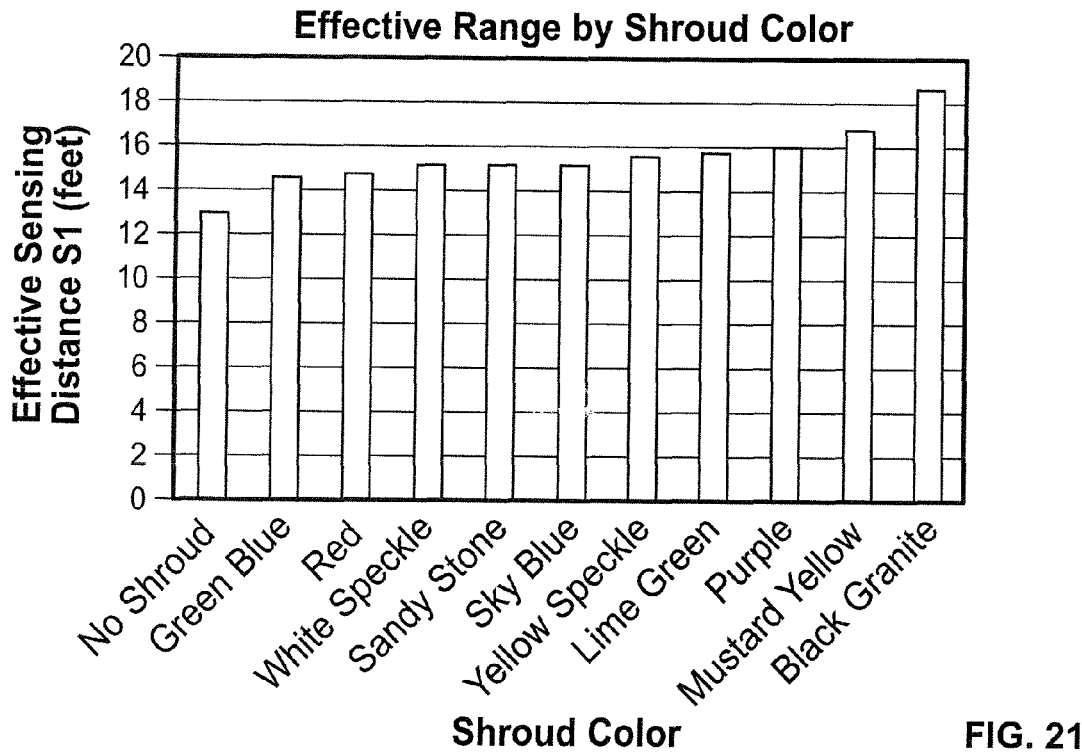

The data collected from the test 400 is shown in FIGS. 19-23. As illustrated in FIGS. 19-21, the sensing capabilities of a dispenser without a shroud is a sensing distance S1 of 13 feet. The sensing distance S1 of the dispenser is greatly improved by adding a shroud of any color around the dispenser. The improved capabilities translate to the sensor being effective for sensing distances of about 14 ft to about 20 ft. Alternatively, the improved capabilities may be generally characterized as an about 7% to about 55% improvement over the sensing distance S1 of dispensers not having a shroud.

Figures 22, 23:
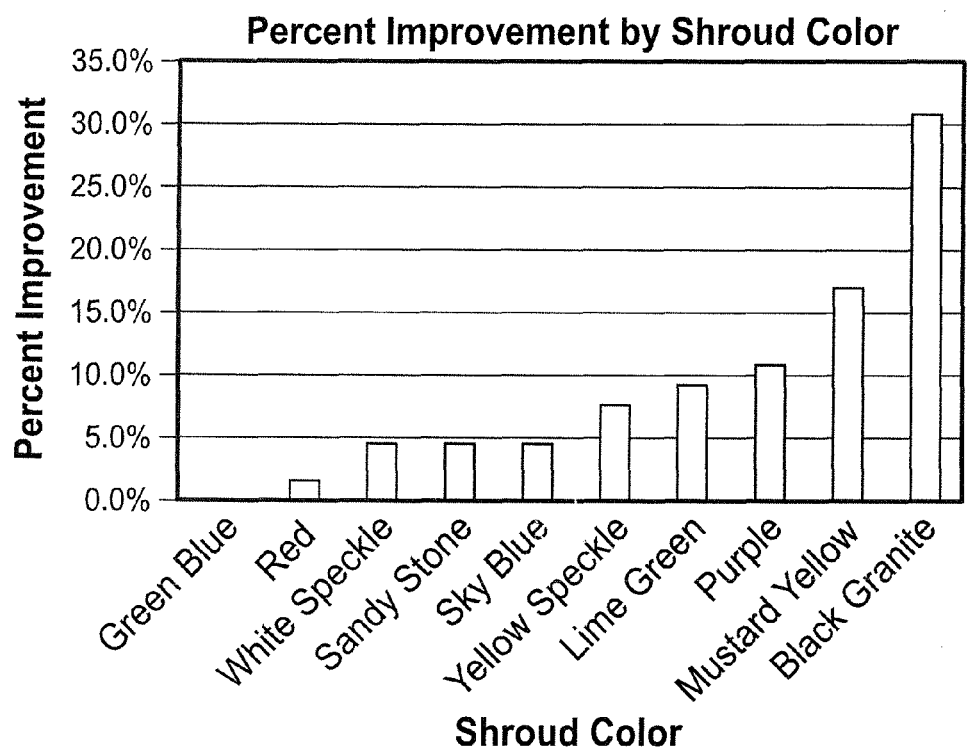
FIGS. 22 and 23 are charts illustrating the results obtained from the test of FIG. 18 normalized for color impact.

FIG. 22 shows the data collected during the test 400 normalized to show how the specific shroud color impacts the overall sensing capabilities of the dispensing system. All of the dispensing systems tested included shrouds having the same sized apertures, structural design, and materials. The only difference in the dispensing systems tested was the color of the shroud enclosing the dispenser. As such, the only difference in the chemical compositions of the various shrouds tested were the dyes used to color the housing. Each color has a specific chemical composition unique to a particular dye. Many materials are selective in their absorption of white light frequencies. The frequencies of the spectrum which are not absorbed are either reflected or transmitted.

As shown in the chart and graph of FIGS. 22 and 23, the shroud with the best sensing capabilities was the black granite colored shroud. The dispensing system with the black granite colored shroud showed a 30.8% improvement in sensor performance from the worst performing dispensing system, i.e., the dispensing system with a green blue colored shroud. Indeed, the testing made clear that several colors resulted in a reduction in background noise of at least 10% when compared to not using a shroud at all. Further, in a specific embodiment at least a 30% reduction in background noise was realized in comparison to not having a shroud.

The results of the testing illustrate how the colored shrouds with greater reflectivity characteristics realized diminished sensor effectiveness in comparison with colored shrouds with less reflective characteristics, i.e., shrouds that absorbed more light, such as the black granite embodiment. The tests suggest that significant background noise is created when light is reflected adjacent the aperture in shrouds that are less light absorptive, which negatively impacts the sensors ability to detect at greater sensing distances.

A test was also conducted to see the relative effects of changing the lux level to the sensing capabilities of dispensers in connection with the addition of a shroud. A sandy stone colored dispenser without a shroud was placed under lights that were increased in intensity from 8000 lux to 15,000 lux. The procedure was then repeated for a dispensing system with a sandy colored shroud. The results of the testing procedure, shown below in Table 1, illustrate that the dispensers with shrouds have an increased sensor effectiveness over the same colored dispenser without the shroud.

TABLE 1

Maximum Detection Distance (feet)

| Lux | Sandy Stone (No Shroud) | Sandy Stone (with Shroud) |
|---|---|---|
| 8000 | 2.7 | 6.7 |
| 10000 | 1.8 | 5.3 |
| 12000 | 0.7 | 3.9 |
| 15000 | 0.1 | 2.5 |

An additional test was conducted to see the relative effects of changing the lux level to the sensing capabilities of dispensing systems with different colored shrouds. Several units were placed under lights that were increased in intensity from 8000 lux to 15,000 lux. It was theorized that the relatively light colored shrouds would reflect significantly more light with this testing protocol adjacent the apertures, which would result in decreased sensor effectiveness. The results of the testing procedure, shown below in Table 2, illustrate the predicted result. The more absorptive colored shroud, i.e., the black speckle embodiment, had the greatest maximum detection distance because of its greater absorption characteristics.

TABLE 2

Maximum Detection Distance (feet)

| Lux | Black Speckle | Sandy Stone | White Speckle |
|---|---|---|---|
| 8000 | 12.4 | 6.7 | 3.7 |
| 10000 | 11.4 | 5.3 | 2.6 |
| 12000 | 9.4 | 3.9 | 0.9 |
| 15000 | 7.8 | 2.5 | 0.2 |

The sensing capabilities, i.e., the effective sensing distance S1 of the sensor can be tailored to specific purposes by merely changing the color of the shroud. Additionally, if it is preferred to use a shroud comprising a generally lighter color, speckling of a darker color can be dispersed within the shroud to help improve the sensing capabilities of the sensor while not dramatically changing the overall color of the shroud. In some embodiments, the speckling dispersed within the shroud may be made using a dye having a chemical composition that reduces the reflective nature of the shroud, but is not visible to the human eye, thereby improving the sensing capabilities of the sensor without affecting the aesthetics of the shroud. Further, it is contemplated that instead of changing the color of the entirety of the shroud, a piece of the shroud located near the sensor may be constructed of a darker color. For example, if it was desirable to use a white shroud having a high reflective nature, a piece of the shroud located nearest the sensor could be dyed black to reduce the reflective nature of the shroud nearest the sensor, thereby enhancing the sensing capabilities of the dispensing system without greatly impacting the overall look of the shroud. Further, the piece of the shroud nearest the sensor may be removable and interchangeable with other pieces of varying colors, thereby allowing a user to adjust the sensing capabilities of the dispensing system based on the user's preference and the environment in which the dispensing system is located.

In another embodiment, if it is not feasible or aesthetically pleasing to change the color of the shroud, an internal lens cover may be disposed over the sensor to help prevent background light noise that passes through the shroud from reaching the sensor. In a different embodiment the thickness t of the shroud sidewall may be increased to decrease the amount of background noise passing through the shroud to the sensor. Additionally, as discussed above, a lens cover may be used around the sensor to prevent background light noise from reaching the sensor. Alternatively, for devices located in smaller spaces such a bathroom, shrouds of lighter colors may be used to allow for a decreased sensing distance S1.

It is beneficial to be able to change the effective sensing distances of sensors by merely changing the shroud because manufacturers can create a single dispenser, which may be transferred to different shrouds for different sensing needs depending on the environment in which the dispenser is located. Indeed, it is an intention of the present disclosure to teach and enable the use of modular systems that allow for entire shrouds or portions of shrouds to be removed from dispensers and replaced with other shrouds or portions of shrouds to be responsive to the demands of users.

Exemplary Embodiment of a Dispensing System

FIGS. 24-28 illustrate one example of a dispensing system 500, which includes a dispenser 502 disposed within a shroud 504. The dispenser 502 is adapted for dispensing the contents of an aerosol container 506, which may include any fluid, volatile material, or product known to those of skill in the art. The dispenser 502 may be one of the devices described in Carpenter et al. U.S. patent application Ser. No. 11/725,402, Furner et al. U.S. patent application Ser. No. 13/302,911, Gasper et al. U.S. patent application Ser. No. 13/607,581, and Baranowski et al. U.S. patent application Ser. No. 13/607,581. The dispenser 502 generally includes a housing 508 that is adapted to receive the aerosol container 506 and batteries 510. The housing 508 also includes an actuator arm 512 and a button 514. In addition, the dispenser 502 also includes a controller 516, a motor 518, and a sensor 520, which are provided within the housing 508 shown schematically in FIG. 25.

Figure 26:
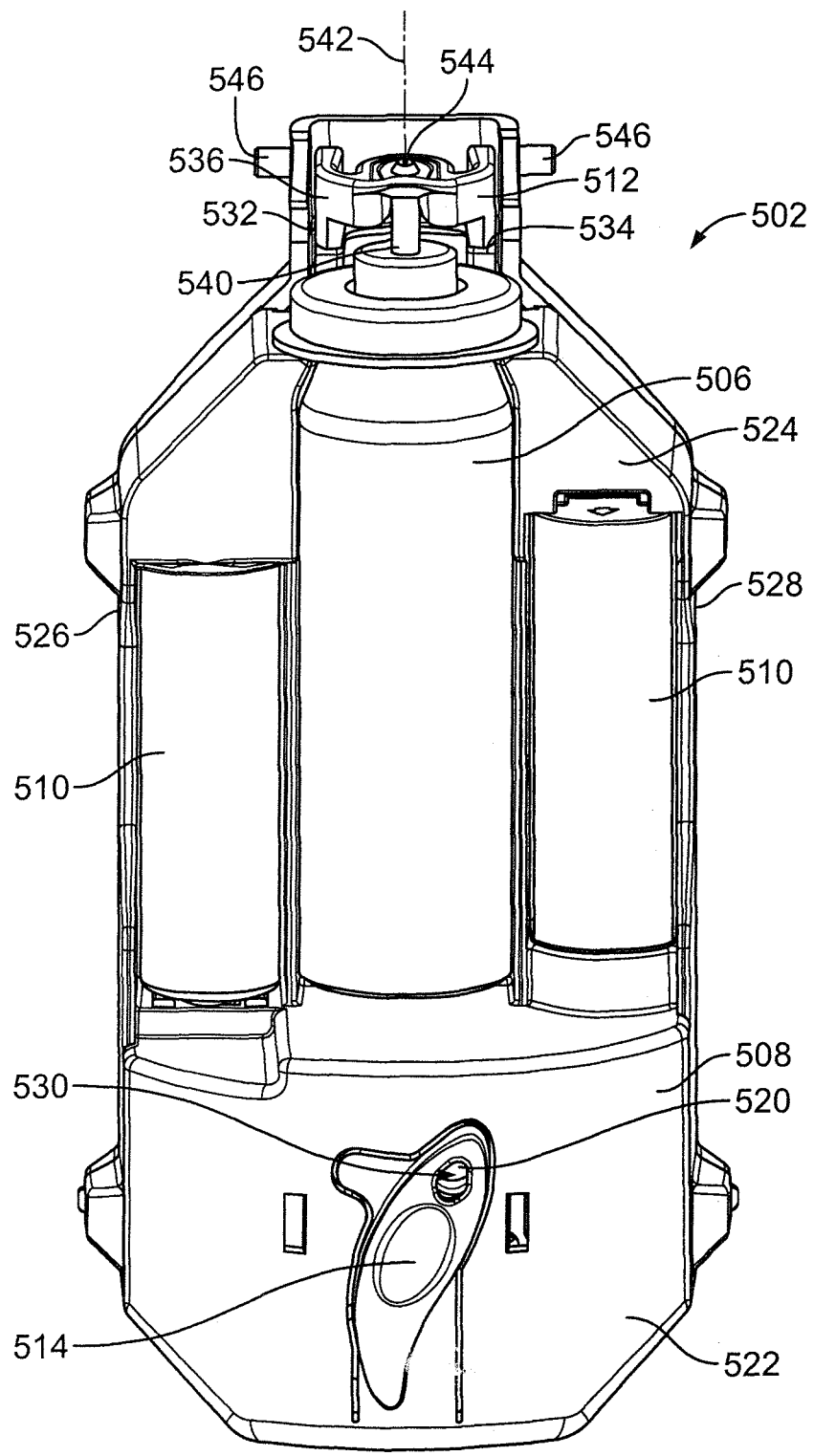
FIG. 26 is a front isometric view of a dispenser for use in the dispensing system of FIG. 24.

Turning now to FIG. 26, the housing 508 of the dispenser 502 comprises a base portion 522, a top portion 524, and first and second sidewalls 526, 528, respectively, extending between the base portion 522 and the top portion 524. The button 514 extends outwardly from the base portion 522 of the housing 508. An aperture 530 is disposed within the button 514. The aperture 530 is aligned with the sensor 520. The button 514 is provided for activating the dispenser 502 to emit product upon depression of same, wherein the depression and/or rotation of the button 514 causes a switch (not shown) to generate a signal and the dispenser 502 to discharge product during manual activation.

The present embodiment also includes an actuator arm cover 532 that extends upwardly from the top portion 524 to cover the actuator arm 512, however, the actuator arm cover 532 may be omitted. As shown in FIG. 26, the actuator arm 512 includes a main portion 534 and an overhang portion 536. The main portion 534 is coupled to a motor by a drive train 538. The overhang portion 536 of the actuator arm 512 extends from the main portion 534 and is substantially transverse to the main portion 534. In a pre-actuation position the overhang portion 536 is positioned slightly above or just in contact with a valve stem 540 of the aerosol container 506. The dispenser 502 discharges product from the container 506 upon occurrence of a particular condition. The condition could be the manual activation of the dispenser 502 or the automatic activation of the dispenser 502 in response to an elapsed time interval or signal from the sensor 520.

Figure 27:
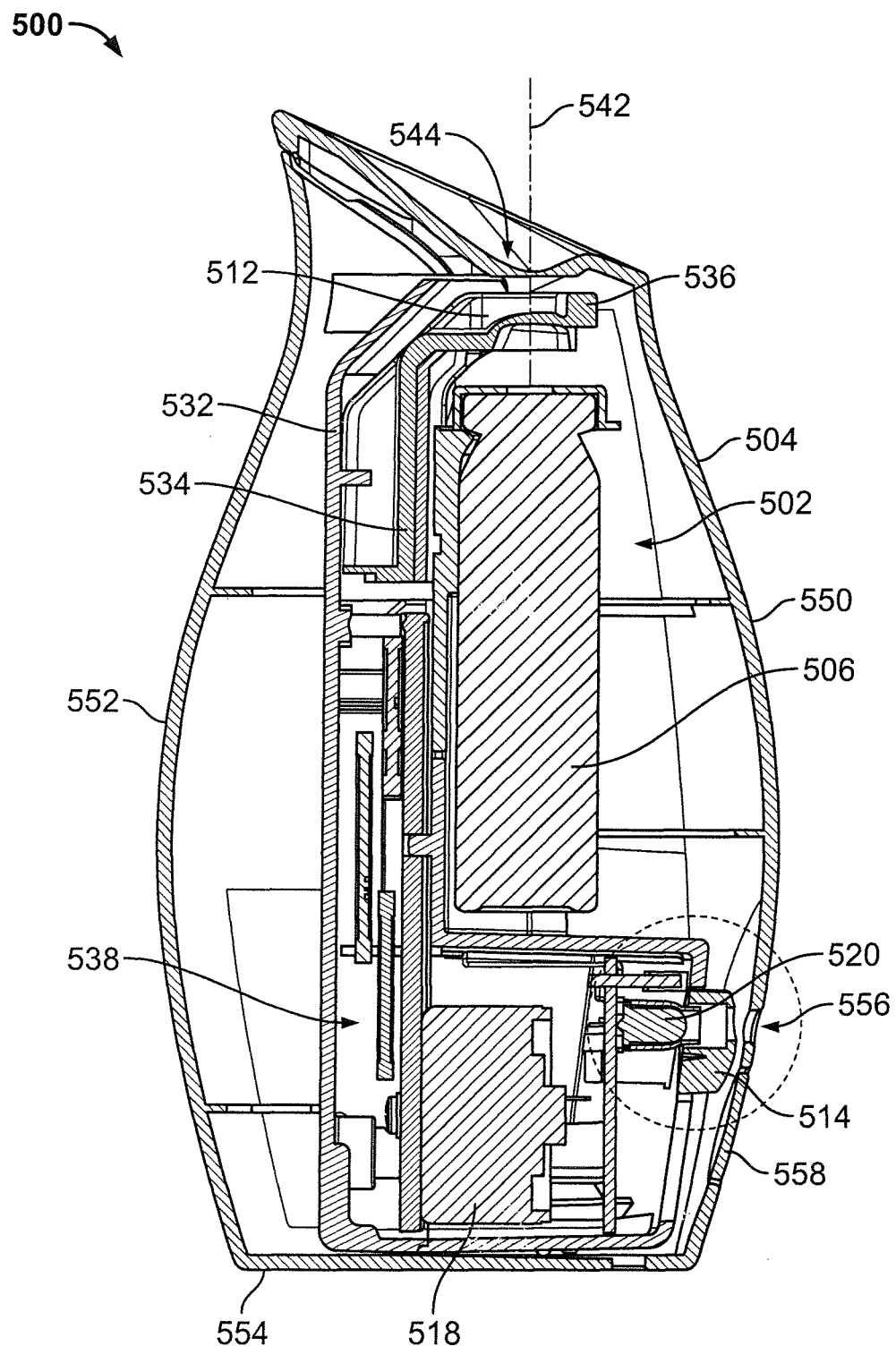
FIG. 27 is a cross-sectional view taken along the line 27-27 of FIG. 24.

Referring to FIGS. 26 and 27, upon the occurrence of a particular condition, the controller 516 activates the motor 518 to pull the actuator arm 512 downwardly in a direction that is parallel to a longitudinal axis 542 of the container 506. Downward movement of the actuator arm 512 depresses the valve stem 540 of the container 506. Depression of the valve stem 540 causes product to be released from the container 506, upwardly through a bore 544 in the overhang portion 536 of the actuator arm 512, and exited upwardly from the dispensing system 500 through an aperture 545 in an upper end of the shroud 504. After product is dispensed from the container 506 the motor 518 is activated to move the actuator arm 512 upwardly to a pre-actuation position. As the actuator arm 512 returns to an upward, unactuated position, the force on the valve stem 540 is removed, thereby closing the valve assembly within the container 506.

Figure 24:
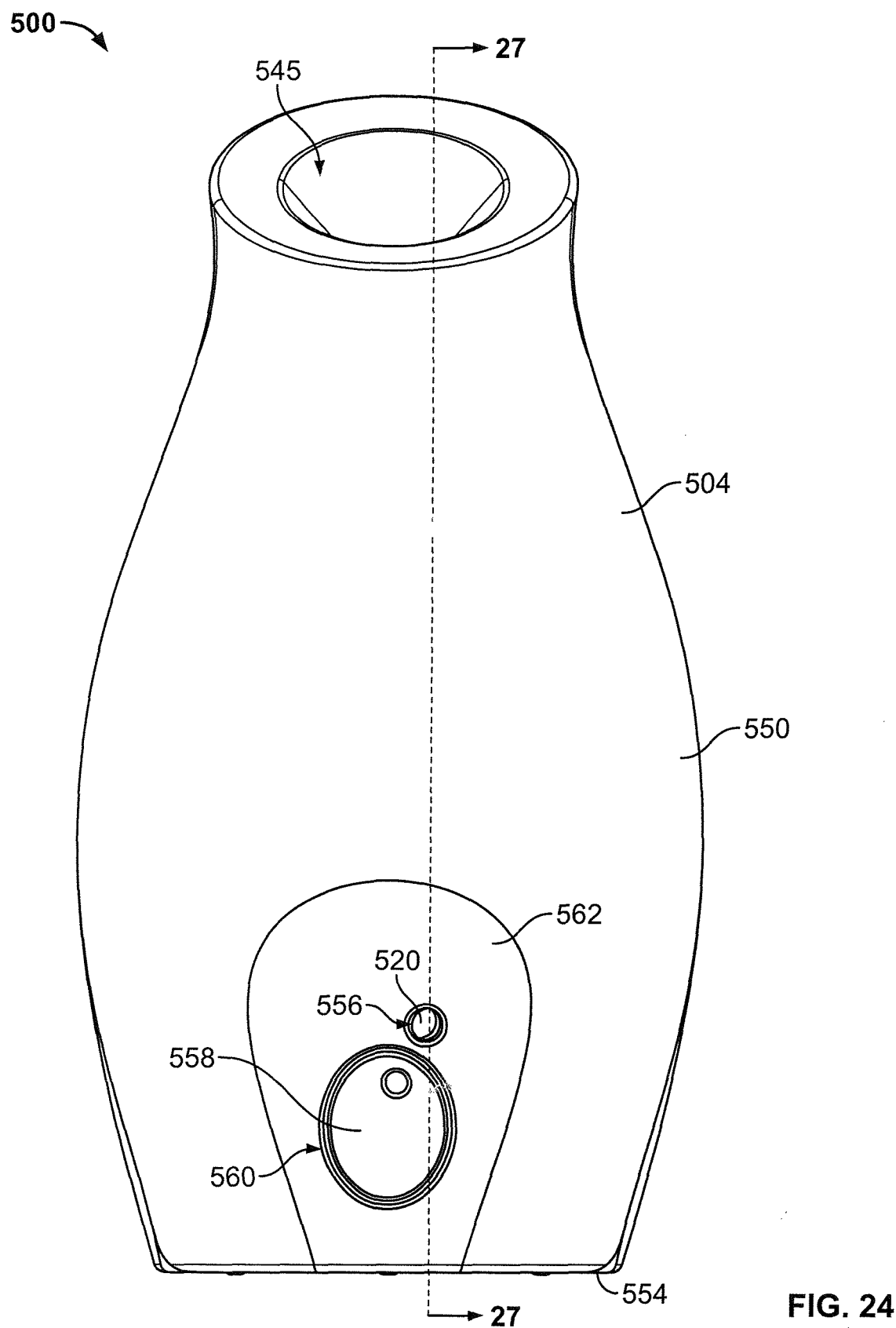
FIG. 24 is a front elevational view of an exemplary embodiment of a dispensing system.
Figure 25:
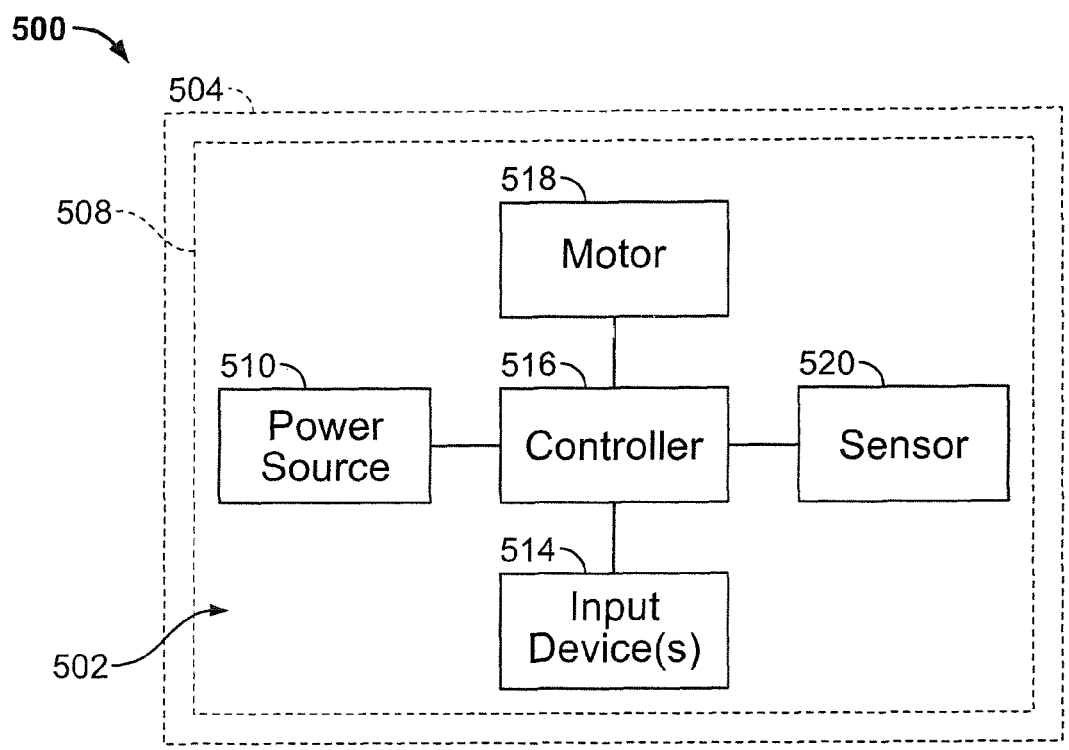
FIG. 25 is a schematic representation of the dispensing system of FIG. 24.

Referring again to FIG. 26, the housing 508 includes two posts 546 extending outwardly from the actuator arm cover 532. The posts 546 are pivotably attached to hinges (not shown) in the shroud 504, to retain the dispenser 502 within the shroud 504. As shown in FIGS. 24 and 27, the shroud 504 is generally tulip-shaped and includes a front portion 550 hingedly attached to a rear portion 552 of the shroud 504 near a bottom end 554 thereof. The front portion 550 is capable of being rotated to an open position to allow access to the dispenser 502 disposed within the shroud 504. The front portion 550 also includes an aperture 556 aligned with the sensor 520 located within the dispenser 502, and a button 558 extending from a similarly shaped aperture 560 in the front portion 550 of the shroud 504. The button 558 is aligned with the button 514 located in the base of the housing 508. The buttons 558 and 514 are aligned such that depression of the button 558 located on the shroud 504 depresses the button 514 on the dispenser 502. In one embodiment, the button 558 and the aperture 556 are both disposed within a modular portion 562 of the shroud 504, such that the modular portion 562 can be removed and replaced with a different modular portion 562 having a differently sized aperture 556. Alternatively, the entire shroud 504 may be removed and replaced with a shroud 504 having a differently sized aperture 556.

Figure 28:
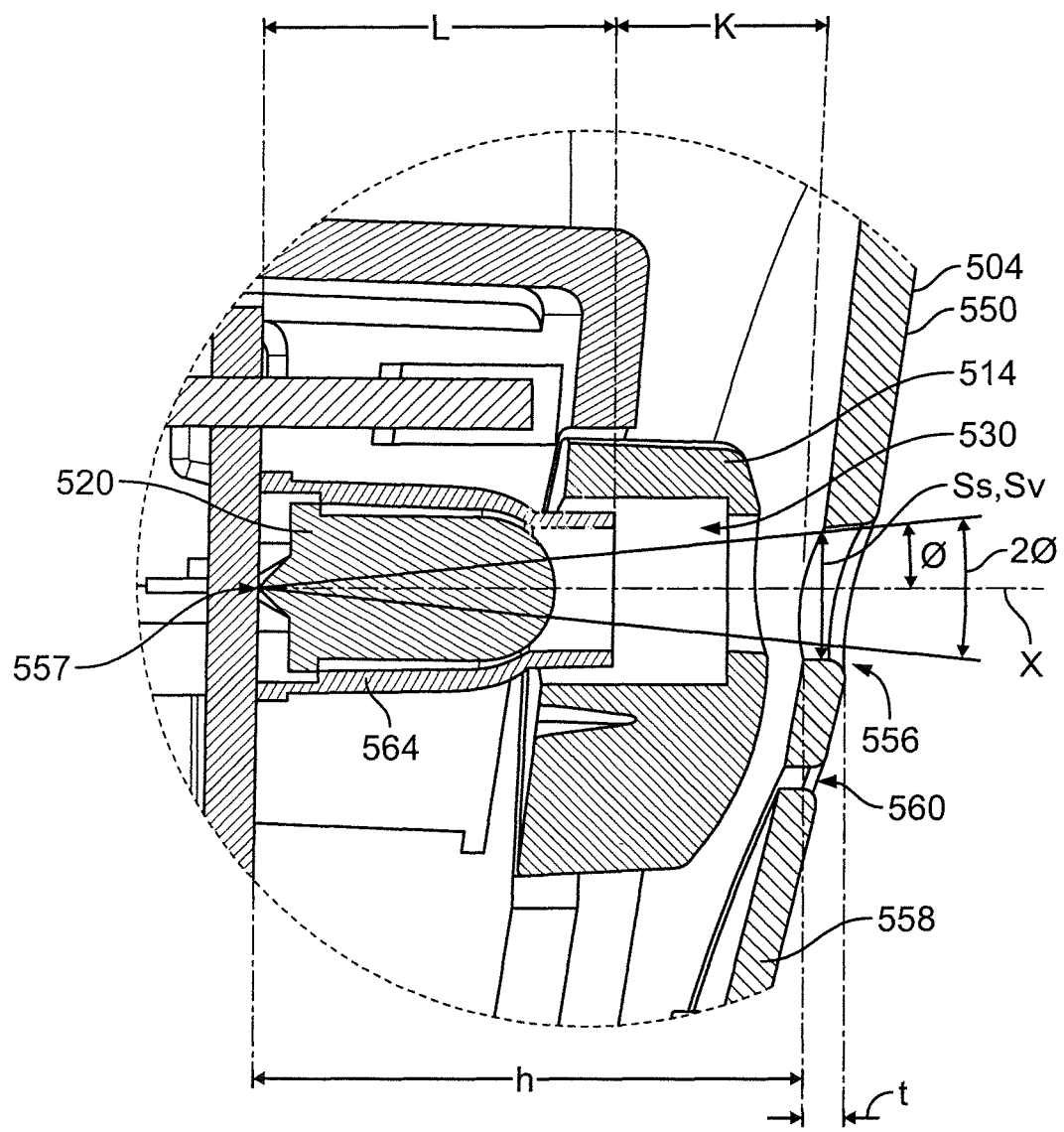
FIG. 28 is an enlarged, partial cross-sectional view of FIG. 27.

Referring now to FIG. 28 the sensor 520 is disposed on the dispenser 502 such that the front focal point 557 of the field of view 2Ø is located a distance h away from the shroud 504, which in the present embodiment is preferably between about 1 to about 50 millimeters, more preferably between about 15 millimeters to about 20 millimeters, and most preferably about 17.58 millimeters. The sensor 520 further includes a lens 564 having a length L of about 1 to about 25 millimeters, more preferably about 10 millimeters to about 12 millimeters, and most preferably about 11.38 millimeters. A distance k defines a virtual shield, which is the difference between the distance h and the lens length L. The distance k is preferably about 1 to about 50 millimeters and more preferably between about 3 to about 10 millimeters. The shroud 504 has a thickness t, which is preferably about 0.5 to about 5 millimeters. The sensor 520 has a field of view of 2Ø, which is preferably between about 5 to about 90 degrees, more preferably 10 to about 30 degrees, and most preferably about 12.33 degrees. A central axis X of the sensor 520 is aligned with the aperture 530 in the button 514 and the aperture 560 in the shroud 504. In the present embodiment, the aperture 556 is sized so that a surface area $S_S$ of the aperture 556 is coincident with a surface area $S_V$ of the field of view 2Ø of the sensor 520. As such, the aperture 556 performance factor $S_A$ is approximately 1 and the sensing capabilities of the dispensing system 500 are maximized.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

We claim:

1. A dispensing system, comprising:
   a dispenser;
   at least one sensor including a lens cover disposed around a portion of the at least one sensor;
   a shroud including at least one aperture; and
   a gap existing between an inner side of the shroud and a distal end of the lens cover,
   wherein a virtual shield is provided in the gap between the distal end of the lens cover and the inner side of the shroud to reduce background noise,
   wherein an aperture performance factor $S_A$ is defined by the ratio $S_A=S_S/S_V$, wherein $S_S$ is a surface area of the at least one aperture in the shroud, and wherein $S_V$ is a field of view surface area of the at least one sensor at an intersection with the shroud, wherein the field of view is defined with a viewing angle wherein the sensitivity drops to 50% of an on-axis sensitivity of the at least one sensor, and
   wherein $S_A \leq 1$.

2. The dispensing system of claim 1, wherein the inner side of the shroud is coincident with the at least one aperture.

3. The dispensing system of claim 2, wherein the at least one sensor has a central axis X extending therethrough that intersects the at least one aperture.

4. The dispensing system of claim 3, wherein a distance between the input end of the sensor and the at least one aperture adjacent the inner wall of the shroud is a distance h about the central axis X.

5. The dispensing system of claim 4, wherein the distance h is between about 15 to about 20 millimeters.

6. The dispensing system of claim 5 wherein the lens cover has a length L between about 10 to about 12 millimeters.

7. The dispensing system of claim 6, wherein a length of the virtual shield is the difference between the distance h and the length L and is between about 3 to about 10 millimeters.

8. A dispensing system, comprising:
   a dispenser having at least one sensor; and
   a shroud including at least one aperture spaced from the at least one sensor and a sensory shield disposed around at least a portion of the at least one sensor, wherein a gap exists between an inner side of the shroud and a distal end of the sensory shield,
   wherein an aperture performance factor $S_A$ is defined by the ratio $S_A=S_S/S_V$, wherein $S_S$ is a surface area of the at least one aperture in the shroud, and wherein $S_V$ is a field of view surface area of the at least one sensor at an intersection with the shroud, wherein the field of view is defined with a viewing angle wherein the sensitivity drops to 50% of an on-axis sensitivity of the at least one sensor, and
   wherein $S_A \leq 1$.

9. The dispensing system of claim 8, wherein $S_A=1$.

10. The dispensing system of claim 8, wherein $S_V > S_S$.

11. The dispensing system of claim 8, wherein the at least one sensor has a viewing angle Ø and is spaced a distance h from the at least one aperture.

12. The dispensing system of claim 11, wherein the at least one aperture is circular and has a diameter D, wherein D=2(h*(tan Ø)) and $S_A=1$.

13. The dispensing system of claim 11, wherein the at least one aperture is circular and has a diameter D, and wherein D<2(h*(tan Ø)) and $S_V > S_S$.

14. The dispensing system of claim 8, wherein $S_S$ defines a circular surface area and $S_V$ defines a circular surface area.

15. The dispensing system of claim 8, wherein $S_S$ defines a non-circular surface area and $S_V$ defines a circular surface area.

16. A dispensing system, comprising:
    a dispenser;
    at least one sensor; and
    a shroud including at least one aperture,
    wherein the shroud is light reflective and includes a colorant that provides a reduction in background noise of at least about 3% when compared to the shroud having a red colorant.

17. The dispensing system of claim 16, wherein the shroud includes a colorant that provides a reduction in background noise of at least about 15% when compared to the shroud having the red colorant.

18. The dispensing system of claim 16, wherein the shroud comprises a thermoplastic material.

* * * * *